(12) United States Patent
Bowler et al.

(10) Patent No.: US 8,791,707 B2
(45) Date of Patent: Jul. 29, 2014

(54) CONCENTRIC COPLANAR CAPACITIVE SENSOR SYSTEM WITH QUANTITATIVE MODEL

(75) Inventors: Nicola Bowler, Ames, IA (US); Tianming Chen, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 398 days.

(21) Appl. No.: 13/185,156

(22) Filed: Jul. 18, 2011

(65) Prior Publication Data
US 2012/0013354 A1 Jan. 19, 2012

Related U.S. Application Data

(60) Provisional application No. 61/365,601, filed on Jul. 19, 2010.

(51) Int. Cl.
*G01N 27/22* (2006.01)
*G01R 27/26* (2006.01)

(52) U.S. Cl.
CPC .................................. *G01N 27/226* (2013.01)
USPC .......................................... 324/658; 324/686

(58) Field of Classification Search
CPC ............... G01R 27/226; G01R 27/228; G01R 27/22–27/2617
See application file for complete search history.

(56) References Cited

U.S. PATENT DOCUMENTS

| | | | |
|---|---|---|---|
| 3,515,987 A * | 6/1970 | Zurbrick et al. .............. | 324/687 |
| 3,706,919 A * | 12/1972 | Abbe ............................ | 361/280 |
| 5,223,796 A | 6/1993 | Waldman et al. | |
| 6,249,130 B1 * | 6/2001 | Greer ............................ | 324/687 |
| 6,426,635 B1 * | 7/2002 | Nussbaum .................... | 324/686 |
| 7,288,945 B2 * | 10/2007 | Martinez et al. .............. | 324/663 |
| 7,554,324 B2 * | 6/2009 | Gualtieri .................. | 324/207.26 |
| 2009/0135157 A1 * | 5/2009 | Harley .......................... | 345/174 |

OTHER PUBLICATIONS

Bord, Isabelle et al., "Influence of the electrodes configuration on a differential capacitive rain sensor performances", Sensors and Actuators B 114 (2006) pp. 640-645.
Li, Xiaobei B. et al., "Design Principles for Multicuhannel Fringing Electric Field Sensors", IEEE Sensors journal, vol. 6, No. 2, Apr. 2006, pp. 434-440.
Mamishev, Alexander V. et al., "Interdigital Sensors and Transducers", Proceedings of IEEE, vol. 92, No. 5, May 2004, pp. 808-845.
Mamishev, Alexander V. et al., "Optimization of Multi-Wavelength Interdigital Dielectrometry Instrumentation and Algorithms", IEEE Transactions on Dielectrics and Electrical Insulation, vol. 5, No. 3, Jun. 1998, pp. 408-420.

(Continued)

*Primary Examiner* — Vinh Nguyen
(74) *Attorney, Agent, or Firm* — McKee, Voorhees & Sease

(57) ABSTRACT

A concentric coplanar capacitive sensor includes a charged central disc forming a first electrode, an outer annular ring coplanar with and outer to the charged central disc, the outer annular ring forming a second electrode, and a gap between the charged central disc and the outer annular ring. The first electrode and the second electrode may be attached to an insulative film. A method provides for determining transcapacitance between the first electrode and the second electrode and using the transcapacitance in a model that accounts for a dielectric test piece to determine inversely the properties of the dielectric test piece.

21 Claims, 18 Drawing Sheets

(56) References Cited

OTHER PUBLICATIONS

Nassr, Amr A. et al., "Coplanar capacitance sensors for detecting water intrusion in composite structures", Measurement Science and Technology, 19 (2008) 075702, pp. 1-7.

Nassr, Amr A. et al., "Non-destructive evaluation of laminated composite plates using dielectrometry sensors" Smart Materials and Structures, 18 (2009) 055014, pp. 1-8.

Shay, I. C. et al., "Cylindrical Geometry Electroquasistatic Dielectrometry" IEEE Transaction on Dielectrics and Electrical Insulation, vol. 12, No. 1, Feb. 2005, pp. 41-49.

Shull, P.J. et al., "Characterization of Capacitive Array for NDE Applications" Res. Nondestr. Eval. (1990) 2:11-27.

Zaretsky, Mark C. et al., "Continuum Properties from Interdigital Electrode Dielectrometry", IEEE Transaction on Electrical Insulation, vol. 23, No. 6, Dec. 1988, pp. 897-917.

J. Baker-Jarvis, et al., "Dielectric and Magnetic Measurements: A Survey of Nondestructive, Quasi-Nondestructive, and Process-Control Techniques", Research in Nondestructive Evaluation, vol. 7, pp. 117-136, 1995.

R.N. Clarke, et al., "Fabry-Perot and open resonators at microwave and millimeter wave frequencies, 2-300 GHz", J. Phys. E: Sci. Instrum., vol. 15, pp. 9-24, 1982.

Jing-Fu Zhao, et al., "Tensor Permittivity Measurements of Thin Films at Millimeter Wavelengths", Intern. J. Infrared and Millimeter Waves, vol. 9, pp. 1093-1105, 1988.

Weiming Ou, et al., "Nondestructive Measurement of a Dielectric Layer Using Surface Electromagnetic Waves", IEEE Trans. Microwave Theory Tech., vol. 31, pp. 255-261, 1983.

R. Olmi, et al., "Diagnostics and monitoring of frescoes using evanescent-field dielectrometry", Meas. Sci. Technol., vol. 17, pp. 2281-2288, 2006.

Robert Comrie, et al., "Nondestructive Examination of Epoxy Adhesive-Bonded Structures Exposed to a Humid Environment: A Comparison of Low- and High-Frequency Dielectric Measurements", J. Adhesion, vol. 78, pp. 967-985, 2002.

Pontus Linderholm, et al., "Bipolar resistivity profiling of 3D tissue culture", Biosensors and Bioelectronics, vol. 22, pp. 789-796, 2007.

W.Q. Yang, et al., "Image reconstruction algorithms for electrical capacitance tomography", Meas. Sci. Technol., vol. 14, pp. R1-R13, 2003.

W.Q. Yang, "Hardware design of electrical capacitance tomography systems", Meas. Sci. Technol., vol. 7, pp. 225-232, 1996.

S.M. Huang, et al., "Design of sensor electronics for electrical capacitance tomography", IEEE Proc.—G, vol. 39, pp. 83-88, 1992.

Lihui Peng, et al., "Determination of the optimal axial length of the electrode in an electrical capacitance tomography sensor", Flow Measurement and Instrumentation, vol. 16, pp. 169-175, 2005.

K.J. Scott., "Electrostatic Potential Green's Functions for Multi-Layered Dielectric Media", Philips J. Research, vol. 45, pp. 293-324, 1990.

J.D. Jackson, "Classical Electrodynamics: Chapter 3—Boundary-Value Problems in Electrostatics: II", John Wiley & Sons, Inc., third edition, 1999.

R.F. Harrington, "Field Computation by Moment Methods: Chapter 7—Eigenvalue Problems", Willey-IEEE Press, 1993.

Tianming Chen, et al., "Analysis of a Concentric Coplanar Capacitive Sensor Using a Spectral Domain Approach", Review of Progress in Quantitative Nondestructive Evaluation, vol. 1335, pp. 1647-1654, 0(Jul. 1, 2010).

\* cited by examiner

US 8,791,707 B2

CONCENTRIC COPLANAR CAPACITIVE SENSOR SYSTEM WITH QUANTITATIVE MODEL

CROSS-REFERENCE TO RELATED APPLICATIONS

This application claims priority under 35 U.S.C. §119 to provisional application Ser. No. 61/365,601 filed Jul. 19, 2010, herein incorporated by reference in its entirety.

GRANT REFERENCE

This invention was made with government support under Grant Nos. NNX07AU54A granted by NASA and FA8650-04-C-5228 granted by U.S. Air Force. The Government has certain rights in the invention.

FIELD OF THE INVENTION

The present invention relates to nondestructive evaluation. More specifically, but not exclusively, the present invention relates to nondestructive evaluation of dielectric materials, including multi-layered dielectric materials, using a capacitive sensor.

BACKGROUND OF THE INVENTION

Dielectric materials play an extensive role in both industrial applications and scientific research areas. In the modern integrated circuit industry, as electrical components are miniaturized, there are palpable needs for dielectric measurements of low-loss thin materials. The use of fine-line signal conductors requires thinner, possibly laminated, low-dielectric constant printed-wiring board materials. On the other hand, compact antenna arrays require high-dielectric constant substrates to obtain phase shifts. Moreover, lightweight structural composites in air- and space-craft, Kevlar body-armor and ceramic-matrix-composites for thermal stability in hot engine environments are examples of some of the recently developed applications of low-conductivity materials. As a result of these increased applications of dielectrics, the quantitative dielectric property characterization of these dielectric materials becomes markedly important for the process control in manufacturing, optimization of electrical apparatus design and performance, and system monitoring and diagnostics.

A number of high frequency nondestructive evaluation (NDE) techniques have been developed for dielectric measurements with their own specific applications [1]. Transmission-line techniques are capable of measuring material permittivity by an open-circuit termination. The material properties of the test-piece can be interpreted from the reflection coefficient of the system. Open resonators have also been used in measuring low-loss materials in the millimeter wavelength range [2] and a certain open resonator system for measuring anisotropic thin films has been developed and is able to obtain the material tensor permittivity values [3]. Measurements using surface electromagnetic waves are quite applicable for low-loss dielectric thin films and layered substrates, since they possess a high quality factor and are therefore sensitive to loss [4]. Evanescent-field dielectrometry has been utilized in diagnosing and monitoring fresco degradations resulting from moisture and soluble salts [5]. Besides, broadband dielectric measurements (0.01 to 3 GHz) on the effects of exposure of thick film adhesive-bonded structures to moisture have been reported [6], where the data obtained are complemented by mechanical testing and failure analysis of the bond structure measured as a function of the exposure time. However, the focus here is on describing electrostatic and low frequency NDE techniques for dielectric measurements.

One important and practical field of material dielectric property characterization is dielectrometry, which derives the complex permittivity of a test-piece from the measured sensor capacitance. Interdigital dielectrometry sensors, with increased effective length and output capacitance between the electrodes because of their interdigital structure, have been used for dielectrometry measurements for a long time. An excellent review paper on interdigital sensors and transducers is [7], in which the physical principles, sensor design and fabrication, and relevant applications of interdigital sensors are discussed in detail. These interdigital dielectrometry sensors have been applied in many fields such as material property monitoring, humidity and moisture sensing, electrical insulation properties sensing, monitoring of curing processes, chemical sensing, biosensing, and so on. For example, using a secant method root-searching routine for parameter estimation, interdigital electrode dielectrometry has been made capable of measuring the continuum parameters of heterogeneous media [8], which include material thickness, material permittivity with thickness known, and material surface conductivity with thickness known. The optimization of multi-wavelength interdigital dielectrometry instrumentation and algorithms has also been described in [9]. Through variation of geometrical design, materials, manufacturing processes, electronic circuitry, and considerations of accumulated effects of non-ideal geometry of experimental setups, improvement of sensor performance can be achieved. Additionally, design principles for multichannel fringing electric field sensors, especially detailed analysis on how the sensor geometry affects the sensor performance and tradeoffs among different design objectives, have been carried out [10] providing insight into design of capacitive sensors in general.

Apart from using interdigital dielectrometry sensors, other sensor configurations have been used to characterize defects, moisture content, temperature, aging status, delamination, and other inhomogeneities in dielectric materials. For example, rectangular capacitive array sensors have been used for the detection of surface and subsurface features in dielectrics and surface features in conductive materials [11]. Cylindrical geometry quasistatic dielectrometry sensors with signal interpretation based on semi-analytical models have also been developed in recent years to measure the permittivity of a dielectric plate [12]. For water intrusion detection in composite structures, rectangular coplanar capacitance sensors with high sensitivity have been developed [13] on the basis that the presence of defects, such as water, leads to changes of dielectric characteristics in the structure, resulting in variations in the sensor measured capacitance. Using a similar principle, rectangular coplanar capacitance sensors have been applied for damage detection in laminated composite plates [14]. Also, the influence of electrode configurations on a differential capacitive rain sensor, which consists of a sensitive capacitor whose capacitance changes in the presence of water and an insensitive reference capacitor, have been investigated in [15]. Moreover, these capacitance techniques have even been employed for the continuous monitoring of the thickness of biofilms and tissue cultures [16].

Electrical capacitance tomography (ECT) is another capacitance measurement technique that is used to image cross-sections of industrial processes containing dielectric materials [17]. The principle is that through image reconstruction for ECT, the test-piece permittivity distribution and therefore the material distribution over its cross-section can be determined. Over the past decades, research progress on both the hardware design [18, 19] and sensor configuration optimization [20] of ECT systems has been made successfully.

Despite these advances in various capacitance measurement techniques, problems remain. What is needed is a sensor and associated methods and systems which can be used in applications, such as, but not limited to quantitative characterization of material properties of multi-layered structures, detection of water or excessive inhomogeneties in structures such as radome structures, and other applications.

BRIEF SUMMARY

Therefore, it is a primary object, feature, or advantage of the present invention to improve over the state of the art.

It is a further object, feature, or advantage of the present invention to provide a sensor and related systems and methods which may be used in quantitative characterization of material properties of multi-layered planar dielectric structures.

Yet a further object, feature, or advantage of the present invention is to provide a sensor and related systems and methods for use in detecting water or excessive inhomogeneities caused by repairs in modern radome structures.

A still further object, feature, or advantage of the present invention is to provide a sensor and related systems and methods which may be used in quantitative characterization of material properties of multi-layered cylindrical dielectric structures.

Another object, feature, or advantage of the present invention is to provide a sensor and related systems and methods which are appropriate for use in handheld devices.

Yet another object, feature, or advantage of the present invention is to provide a rotationally-invariant capacitive probe.

A still further object, feature, or advantage of the present invention is to provide for capacitive probes that allow removal of parasitic capacitances.

The present invention is not to be limited to or by these objects, features, and advantages. It is to be further understood that no single embodiment of the present invention need exhibit all of these objects, features, or advantages.

According to one aspect of the present invention, a concentric coplanar capacitive sensor is provided. The sensor includes a charged central disc forming a first electrode and an outer annular ring coplanar with and outer to the charged central disc, the outer annular ring forming a second electrode. There is a gap between the charged central disc and the outer annular ring. The first electrode and the second electrode are attached to an insulative film.

According to another aspect of the present invention, a capacitive nondestructive evaluation system for evaluating a dielectric test piece is provided. The system includes a concentric coplanar capacitive sensor having (a) a charged central disc forming a first electrode, (b) an outer annular ring coplanar with and outer to the charged central disc, the outer annular ring forming a second electrode, and (c) a gap between the charged central disc and the outer annular ring. The system also includes a capacitance measuring circuit electrically connected to the concentric coplanar capacitive sensor for measuring transcapacitance between the first electrode and the second electrode for use in evaluating the dielectric test piece.

According to another aspect of the present invention, a method of non-destructive evaluation is provided. The method includes providing a concentric coplanar capacitive sensor, attaching the concentric coplanar capacitive sensor to a dielectric test piece, applying an input signal across the concentric coplanar capacitive sensor to produce an output signal, determining transcapacitance between the first electrode and the second electrode based on the output signal, and using the transcapacitance in a model that accounts for the dielectric test piece to determine inversely the properties of the dielectric test piece.

BRIEF DESCRIPTION OF THE DRAWINGS

FIG. 15A is an experiment setup used in probe lift-off measurements; FIG. 15B is a concentric capacitive sensor fabricated by photolithography.

FIG. 17A is a cross-section view of a concentric capacitive sensor in surface contact with a one-layer dielectric in free space. FIG. 17B is a calculated sensor output capacitance as a function of test-piece permittivity and thickness. FIG. 17C is a calculated difference between the capacitance in FIG. 17B and that of a similar but infinitely thick test-piece.

FIG. 18A illustrates stepped Delrin® slab $\in_r$=3.82; FIG. 18B illustrates stepped HDPE slab $\in_r$=2.65. FIGS. 18C and 18D illustrate difference calculated for Delrin® and HDPE respectively, assuming an 18-mm-thick test-piece to be an approximate half-space FIGS. 19A-19D measured and calculated differences in capacitance of hand-held probes as a function of liftoff.

FIG. 21A is sensor A and injected water. FIG. 21B is sensor A and injected olive oil. FIG. 21C is sensor B and injected water. FIG. 21D is sensor B and injected olive oil.

DETAILED DESCRIPTION OF THE PREFERRED EMBODIMENT

1. Introduction

The present invention provides for a concentric coplanar capacitive sensor which may be used for detecting water or excessive inhomogeneities caused by repairs in modern radome structures. The proposed sensor, having the advantage of rotational symmetry, consists of a charged central disc and a coplanar outer annular ring that exhibit a measurable transcapacitance $C_T$. The output signal depends on the material and structural properties of the test-piece with which the sensor is in surface contact. An electrostatic Green's function for a three-layered dielectric structure in free space is derived in cylindrical coordinates through the Hankel transform method. This derived Green's function may then be simplified, providing results for many other cases such as a half-space dielectric, a layered half-space dielectric, and one- and two-layered dielectrics in free space. Numerical implementations based on these Green's functions are described, in which the surface charge distribution on the sensor electrodes is calculated through the method of moments (MoM). From the surface charge, $C_T$ is calculated. To verify the validity of the numerical calculation, benchmark experiments are conducted for one-, two-, and three-layer dielectric test-pieces in free space, respectively. Very good agreement is observed between the calculated and measured transcapacitance. Furthermore, water ingression measurements in a sandwich structure are carried out and demonstrate the feasibility of using the capacitive sensor to detect water intrusion and inhomogeneities in radome structures.

2. Green's Functions for Multilayered Dielectrics

Figure 1:
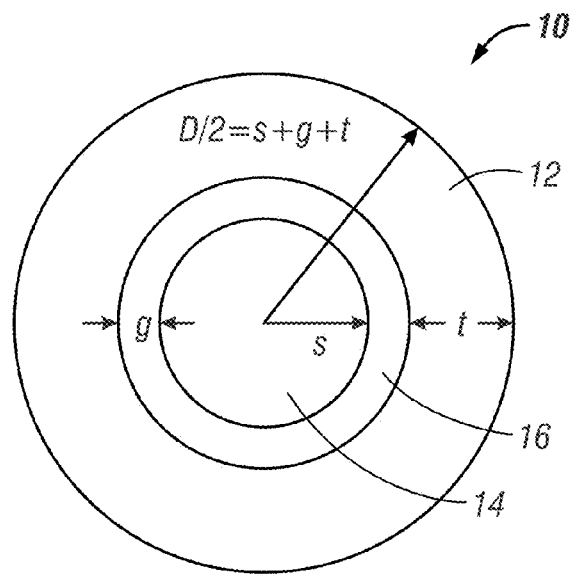
FIG. 1 illustrates a concentric coplanar capacitive sensor. The radius of the central disc and the width of the outer ring are denoted s and t, respectively. The gap between them is g, and D is the sensor diameter

The configuration of the proposed sensor is shown in FIG. 1. In FIG. 1, a concentric coplanar capacitive sensor 10 is shown having a charged central disc 14. There is an outer annular ring 12 which is coplanar with and outer to the charged central disc 14. There is a gap 16 between the charged central disc 14 and the outer annular ring 12.

Electrostatic Green's functions due to a point charge over different test-piece structures are derived first. These Green's functions are then utilized in later MoM calculations of the sensor transcapacitance $C_T$. Because of the cylindrical symmetry of the designed sensor, the electrostatic Green's functions are derived in cylindrical coordinates through the Hankel transform method. Additionally, the test-pieces in our theoretical analyses are assumed to be infinite in the horizontal directions and the sensor electrodes are assumed to be infinitesimally thin.

Assume there is a point charge placed at the origin in free space. The resulting electrostatic potential $\Psi$, related to the electric field $E=-\nabla\Psi$, satisfies the Laplace equation and can be expressed in cylindrical coordinates as $$\left(\frac{\partial^2}{\partial\rho^2} + \frac{1}{\rho}\frac{\partial}{\partial\rho} + \frac{\partial^2}{\partial z^2}\right)\Psi(\rho, z) = 0, \ r \neq 0 \quad (1)$$

where $\Psi(\rho, z)$ is independent of azimuthal angle $\phi$. Next, the Hankel transform $\tilde{f}(\kappa)$ of zero-order of a function $f(\rho)$ is given by $$\tilde{f}(\kappa) = \int_0^\infty f(\rho) J_0(\kappa\rho) \rho d\rho \quad (2)$$

where $J_0(z)$ is the Bessel function of the first kind and the inverse transform is of the same form. Apply the zero-order Hankel transform to equation (1), making use of the following identity $$\int_0^\infty \left[\left(\frac{\partial^2}{\partial\rho^2} + \frac{1}{\rho}\frac{\partial}{\partial\rho}\right)f(\rho)\right] J_0(\kappa\rho)\rho d\rho = -\kappa^2 \tilde{f}(\kappa), \quad (3)$$

where $f(\rho)$ is assumed to be such that the terms $\rho J_0(\kappa\rho)\partial f(\rho)/\partial\rho$ and $\rho f(\rho)\partial J_0(\kappa\rho)/\partial\rho$ vanish at both limits. The spatial domain Laplace equation (1) is then transformed into a one-dimensional Helmholtz equation in the transformed domain:

$$\left(\frac{\partial^2}{\partial z^2} - \kappa^2\right)\tilde{\Psi}(\kappa, z) = 0 \quad (4)$$

where for $\kappa$ the root with positive real part is taken. Here, the Green's functions are first derived in the transformed domain and then transformed back to the spatial domain through the inverse Hankel transform.

The present invention further contemplates that sensor surface charge density may be computed in alternative ways. For example, the spectral domain Green's function may be used to derive the integral equation for the sensor surface charge density in the spectral domain, using Parseval's theorem. Then the integral equation may be discretized to form matrix equations using the MoM. The spatial domain approach is more computationally efficient for both one- and three-layered structures in free space, while the Green's function derivation and numerical implementation for the spectral domain approach are more straightforward. Additional details regarding the alternative approach are described in [24].

2.1 Point Charge on Top of a Four-Layer Dielectric

Figure 2:
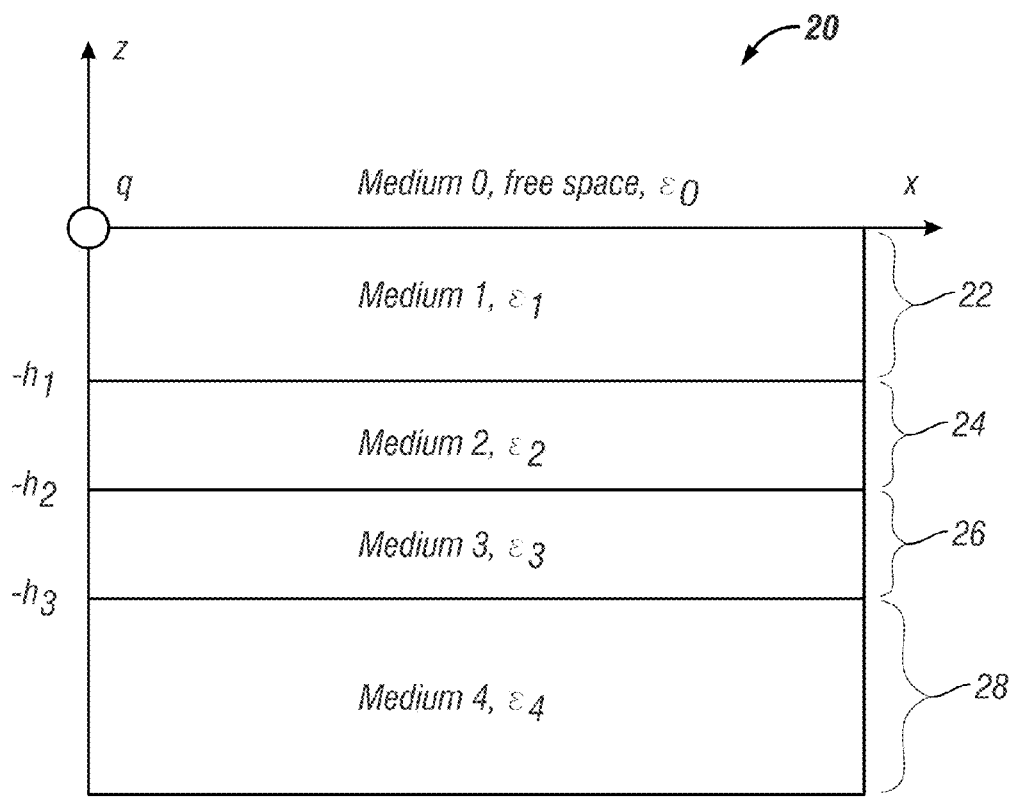
FIG. 2 illustrates a point charge on top of a four-layer dielectric.

One potential application of the capacitive sensor is the dielectric property characterization of three-layer modern aircraft radome structures, using the knowledge of sensor geometry and the output transcapacitance $C_T$. In order to set up the governing equations in the MoM calculations for the in-contact characterization of layered dielectric structures, the potential due to a point charge in the plane z=0 is derived. Without loss of generality, a four-layer half-space dielectric configuration shown in FIG. 2 is used in the following theoretical derivation. One can easily obtain the solution for the three-layer radome structure by replacing $\in_4$ by $\in_0$, the permittivity of free space.

In FIG. 2, a point charge is placed on top of a four-layer half-space dielectric. The electrostatic potential $\Psi$ satisfies the Laplace equation in each homogeneous medium. After applying the zero-order Hankel transform mentioned above, the resulting one-dimensional Helmholtz equations in the transformed domain can be expressed as $$\left(\frac{\partial^2}{\partial z^2} - \kappa^2\right)\Psi_0(\kappa, z) = \frac{1}{2\pi}\delta(z), \quad z \geq 0 \tag{5}$$

$$\left(\frac{\partial^2}{\partial z^2} - \kappa^2\right)\Psi_i(\kappa, z) = 0 \tag{6}$$
$$-h_i \leq -h_{i-1}$$

where i=1, 2, 3, 4, and $h_0$=0 while $h_4 \to -\infty$. The subscripts 0, 1, ..., 4 denote the free space above the dielectric and each homogeneous layer of the dielectric, respectively. From equations (5) and (6), general solutions for the potentials in each region can be expressed as $$\Psi_i(\kappa,z) = A_i(\kappa)e^{-\kappa z} + B_i(\kappa)e^{\kappa z}, \quad -h_i \leq z \leq -h_{i-1}, \tag{7}$$

where $B_0(\kappa) = A_4(\kappa) = 0$ due to the fact that the potential at infinity vanishes.

The interface conditions on the electric fields are $$\hat{z} \times (E_0 - E_1) = 0, \hat{z} \cdot (D_0 - D_1) = \rho_s \tag{8}$$

$$\hat{z} \times (E_i - E_{i+1}) = 0, \hat{z} \cdot (D_i - D_{i+1}) = 0 \tag{9}$$

where i=1, 2, 3, and $\rho_s$ is the free surface charge density in the plane z=0. Applying the Hankel transform to the interface conditions for E and D, the corresponding boundary conditions for the potentials in the transformed domain are expressed:

$$\Psi_0(\kappa, 0) = \Psi_1(\kappa, 0), \tag{10}$$

$$-\varepsilon_0 \frac{\partial \Psi_0(\kappa, 0)}{\partial z} + \varepsilon_1 \frac{\partial \Psi_1(\kappa, 0)}{\partial z} = \frac{1}{2\pi}, \tag{11}$$

$$\Psi_i(\kappa, -h_i) = \Psi_{i+1}(\kappa, -h_i), \tag{12}$$

$$\varepsilon_i \frac{\partial \Psi_i(\kappa, -h_i)}{\partial z} = \varepsilon_{i+1} \frac{\partial \Psi_{i+1}(\kappa, -h_i)}{\partial z} \tag{13}$$

where i=1, 2, 3. A little more explanation is made here about the $\frac{1}{2\pi}$ term on the right-hand side of equation (11). In cylindrical coordinates, the Dirac delta-function can be expressed for points on the z axis as $$\delta(r - r') = \frac{1}{2\pi\rho}\delta(\rho)\delta(z - z') \tag{14}$$

Therefore, the surface charge density in the plane z=0 is $\rho_s = \delta(\rho)/2\pi\rho$, with its Hankel transform being $\frac{1}{2\pi}$. Applying the Hankel transform to the boundary condition equation (8), one can easily get the result shown in equation (11).

Substitute equation (7) into equations (10) to (13) to express the coefficient $A_1(\kappa)$ as $$A_1(\kappa) = \tag{15}$$

$$-\frac{1}{2\pi\kappa(\varepsilon_0 + \varepsilon_1)} \times \lfloor \delta e^{-2\kappa h_3} + \gamma e^{-2\kappa h_2} + \beta e^{-2\kappa h_1} + \beta\gamma\delta e^{-2\kappa(h_1 + h_3 - h_2)} \rfloor \times$$

$$\sum_{n=0}^{\infty} (-1)^n \frac{(\beta + \alpha e^{-2\kappa T_1})^n}{(1 + \alpha\beta e^{-2\kappa T_1})^{n+1}} \frac{(\gamma + \delta e^{-2\kappa T_3})^n}{(1 + \gamma\delta e^{-2\kappa T_3})^{n+1}} e^{-2\kappa n T_2},$$

where $\alpha = (\in_1 - \in_0)/(\in_1 + \in_0)$, $\beta = (\in_2 - \in_1)/(\in_2 + \in_1)$, $\gamma = (\in_3 - \in_2)/(\in_3 + \in_2)$, $\delta = (\in_4 - \in_3)/(\in_4 + \in_3)$. Besides, $T_1 = h_1$, $T_2 = h_2 - h_1$, and $T_3 = h_3 - h_2$. In order to get the spatial domain solution, equation (15) can be expanded into the form of series summations, which facilitates application of the inverse Hankel transform. For those terms inside the summation of $A_1(\kappa)$, we have $$(\beta + \alpha e^{-2\kappa T_1})^n = \sum_{r=0}^{n} \frac{n!}{r!(n-r)!}\beta^{n-r}\alpha^r e^{-2r\kappa T_1}, \tag{16}$$

$$\frac{1}{(1 + \alpha\beta e^{-2\kappa T_1})^{n+1}} = \sum_{s=0}^{\infty}(-1)^s \frac{(n+s)!}{n!s!}(\alpha\beta)^s e^{-2s\kappa T_1}, \tag{17}$$

and similarly for terms $(\gamma + \delta e^{-2\kappa T_3})^n$ and $(1 + \gamma\delta e^{-2\kappa T_3})^{-(n+1)}$. Combining equations (16) and (17) gives $$\frac{(\beta + \alpha e^{-2\kappa T_1})^n}{(1 + \alpha\beta e^{-2\kappa T_1})^{n+1}} = \sum_{s=0}^{\infty}\sum_{r=0}^{n}(-1)^s \frac{(n+s)!}{r!(n-r)!s!}\alpha^{r+s}\beta^{n+s-r}e^{-2(r+s)\kappa T_1}. \tag{18}$$

Adopting m=r+s, equation (18) is then written in the following form $$\frac{(\beta + \alpha e^{-2\kappa T_1})^n}{(1 + \alpha\beta e^{-2\kappa T_1})^{n+1}} = \sum_{m=0}^{\infty} K_{mn}(\alpha, \beta)e^{-2\kappa m T_1} \tag{19}$$

where $$K_{mn}(\alpha, \beta) = \sum_{r=0}^{min(m,n)}(-1)^{m-r} \times \frac{(m+n-r)!}{r!(m-r)!(n-r)}\alpha^m \beta^{m+n-2r}. \tag{20}$$

Similarly $$\frac{(\gamma + \delta e^{-2\kappa T_3})^n}{(1 + \gamma\delta e^{-2\kappa T_3})^{n+1}} = \sum_{l=0}^{\infty} K_{ln}(\delta, \gamma)e^{-2\kappa l T_3}. \tag{21}$$

Finally, the series summation form for $A_1(\kappa)$ in the transformed domain is written as $$A_1(\kappa) = \tag{22}$$

-continued $$-\frac{1}{2\pi\kappa(\varepsilon_0+\varepsilon_1)}[\delta e^{-2\kappa h_3}+\gamma e^{-2\kappa h_2}+\beta e^{-2\kappa h_1}+\beta\gamma\delta e^{-2\kappa(h_1+h_3-h_2)}]\times$$

$$\sum_{n=0}^{\infty}\sum_{l=0}^{\infty}\sum_{m=0}^{\infty}(-1)^n K_{mn}(\alpha,\beta)K_{ln}(\delta,\gamma)e^{-2\kappa mT_1}e^{-2\kappa nT_2}e^{-2\kappa lT_3},$$

and it is found from the boundary conditions that $$A_0(\kappa)=\frac{1}{2\pi\kappa(\varepsilon_0+\varepsilon_1)}+(1+\alpha)A_1(\kappa) \tag{23}$$

Applying the inverse Hankel transform to equation (23), the potential in the z=0 plane due to a point charge at the origin is expressed as $$\Psi_0(\rho,0)=\frac{1}{2\pi(\varepsilon_0+\varepsilon_1)\rho}+(1+\alpha)\int_0^{\infty}A_1(\kappa)J_0(\kappa\rho)\kappa\,d\kappa. \tag{24}$$

The integral in equation (24) can be evaluated by applying the following Hankel transform pair to each of its power series terms, given in equation (22), $$\int_0^{\infty}\frac{e^{-\kappa z}}{\kappa}J_0(\kappa\rho)\kappa\,d\kappa=\frac{1}{\sqrt{\rho^2+z^2}} \tag{25}$$

Equation (24) is finally expressed in real-space form as $$\Psi_0(\rho,0)=\frac{1}{2\pi(\varepsilon_0+\varepsilon_1)\rho}-\frac{1+\alpha}{2\pi(\varepsilon_0+\varepsilon_1)}(G_1+G_2+G_3+G_4), \tag{26}$$

where $$G_1=\sum_{n=0}^{\infty}\sum_{l=0}^{\infty}\sum_{m=0}^{\infty}(-1)^n K_{mn}(\alpha,\beta) \tag{27}$$

$$K_{ln}(\delta,\gamma)\times\frac{\delta}{\sqrt{\rho^2+[2(mT_1+nT_2+lT_3+h_3)]^2}},$$

$$G_2=\sum_{n=0}^{\infty}\sum_{l=0}^{\infty}\sum_{m=0}^{\infty}(-1)^n K_{mn}(\alpha,\beta) \tag{28}$$

$$K_{ln}(\delta,\gamma)\times\frac{\gamma}{\sqrt{\rho^2+[2(mT_1+nT_2+lT_3+h_2)]^2}},$$

$$G_3=\sum_{n=0}^{\infty}\sum_{l=0}^{\infty}\sum_{m=0}^{\infty}(-1)^n K_{mn}(\alpha,\beta) \tag{29}$$

$$K_{ln}(\delta,\gamma)\times\frac{\beta}{\sqrt{\rho^2+[2(mT_1+nT_2+lT_3+h_1)]^2}},$$

$$G_4=\sum_{n=0}^{\infty}\sum_{l=0}^{\infty}\sum_{m=0}^{\infty}(-1)^n K_{mn}(\alpha,\beta)K_{ln}(\delta,\gamma)\times \tag{30}$$

$$\frac{\beta\gamma\delta}{\sqrt{\rho^2+[2(mT_1+nT_2+lT_3+h_1+h_3-h_2)]^2}}$$

Equations (26) to (30) together give the surface potential $\Psi_0(\rho,0)$ due to a point charge at the surface of a four-layer half-space dielectric in the spatial domain. The potential throughout the entire domain can be derived from the above equations but only $\Psi_0(\rho,0)$ is needed here for later MoM calculations because the sensor is in contact with the test-piece surface. By substituting $\varepsilon_0$ for $\varepsilon_4$ in the above relations, the potential due to a point charge on top of a three-layer dielectric in free space can be retrieved. Numerical results based on this potential are compared with corresponding experimental results in Section 4.

2.2 Point Charge on Top of a Two-Layer Dielectric in Free Space

The surface potential for the case of a point charge on top of a two-layer dielectric can be simplified from equation (26) by assuming that $\varepsilon_1=\varepsilon_2$ and $\varepsilon_4=\varepsilon_0$. We are interested in this case for the purpose of benchmark testing described in Section 4. As a result, $\beta$ becomes zero and $G_3=G_4=0$. On the other hand, $\kappa_{mn}(\alpha,\beta)$ has a non-zero value, $\kappa_{mn}(\alpha)=\alpha^n$, only when m=n=r. This is because when m≠n, the term m+n−2r is constantly greater than zero and thus $\beta^{m+n-2r}=0$. Hence, the corresponding potential is simplified as $$\Psi_0(\rho,0)=\frac{1}{2\pi(\varepsilon_0+\varepsilon_1)\rho}-\frac{1+\alpha}{2\pi(\varepsilon_0+\varepsilon_1)}(G_1+G_2), \tag{31}$$

where $$G_1= \tag{32}$$

$$\sum_{n=0}^{\infty}\sum_{m=0}^{\infty}(-1)^n\alpha^n K_{mn}(\delta,\gamma)\times\frac{\delta}{\sqrt{\rho_2+\{2[(n+1)T_1+(m+1)T_2]\}^2}},$$

$$G_2=\sum_{n=0}^{\infty}\sum_{m=0}^{\infty}(-1)^n\alpha^n K_{mn}(\delta,\gamma)\times\frac{\delta}{\sqrt{\rho^2+\{2[(n+1)T_1+mT_2]\}^2}}. \tag{33}$$

Here, $T_1$ and $T_2$ represent the thickness of the top and bottom homogeneous layers, respectively.

2.3 Point Charge on Top of a Two-Layer Half-Space Dielectric

The above derived potential due to a point charge over the surface of a four-layer half-space dielectric can also be reduced to the case of a point charge on top of a coated half-space dielectric. This case can be furthermore reduced to the solutions of a point charge on top of a one-layer dielectric slab in free space and a point charge on top of a homogeneous half-space dielectric. These simplified results are identical to those presented in [21] and [22]. In addition, calculation results based on the potential due to a point charge on top of a one-layer dielectric in free space are used in the benchmark comparison in Section 4.

Figure 3:
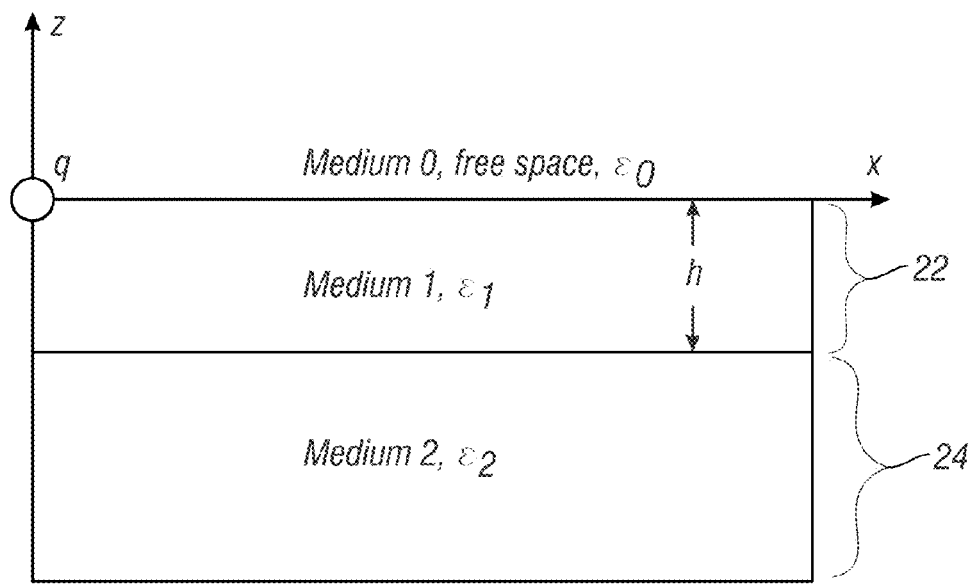
FIG. 3 illustrates a point charge on top of a layered half-space dielectric.

Assuming that $\varepsilon_1=\varepsilon_2=\varepsilon_3\neq\varepsilon_0$, the structure in FIG. 2 is simplified into the case of a half-space dielectric with a single surface layer as shown in FIG. 3. The top layer has dielectric constant $\varepsilon_1$ and thickness h. The bottom layer is the half-space dielectric with dielectric constant $\varepsilon_2$. In this case, $\beta=\gamma=0$. $\kappa_{mn}(\alpha,\beta)$ only has non-zero value when m=n=r and $\kappa_{mn}(\alpha)=\alpha^n$. Similarly, $\kappa_{ln}(\delta,\gamma)$ only has non-zero value when l=n=t and $\kappa_{ln}(\delta)=\delta^n$. Equation (26) is simplified to $$\Psi_0(\rho, 0) = \quad (34)$$

$$\frac{1}{2\pi(\varepsilon_0 + \varepsilon_1)} \times \left\{ \frac{1}{\rho} - (1+\alpha) \sum_{n=0}^{\infty} (-1)^n \frac{(\alpha)^n (\delta)^{n+1}}{\sqrt{\rho^2 + [2(n+1)h]^2}} \right\},$$

where $\alpha = (\varepsilon_1 - \varepsilon_0)/(\varepsilon_1 + \varepsilon_0)$ and $\delta = (\varepsilon_2 - \delta_1)/(\varepsilon_2 + \varepsilon_1)$. To compare the derived result with that in the literature, rewrite equation (34) in terms of coefficients $\alpha = (\varepsilon_1 - \varepsilon_0)/(\varepsilon_1 + \varepsilon_0)$ and $\beta = (\varepsilon_1 - \varepsilon_2)/(\varepsilon_2 + \varepsilon_1)$, which gives $$\Psi_0(\rho, 0) = \quad (35)$$

$$\frac{1}{2\pi(\varepsilon_0 + \varepsilon_1)} \times \left\{ \frac{1}{\rho} + (1+\alpha) \sum_{n=0}^{\infty} (\alpha\beta)^n \frac{\beta}{\sqrt{\rho^2 + [2(n+1)h]^2}} \right\}.$$

Equation (35) is identical with the result presented in [21], where the Green's function is derived using a double Fourier transform in Cartesian coordinates.

A special case is that in which the half-space dielectric is replaced by free space and the test-piece in contact with the sensor is then a homogeneous plate. The corresponding potential is expressed in equation (36) by replacing $\varepsilon_2$ with $\varepsilon_0$ in equation (35):

$$\Psi_0(\rho, 0) = \quad (36)$$

$$\frac{1}{2\pi(\varepsilon_0 + \varepsilon_1)} \times \left\{ \frac{1}{\rho} + (1+\alpha) \sum_{n=0}^{\infty} \alpha^{2n+1} \frac{\beta}{\sqrt{\rho^2 + [2(n+1)h]^2}} \right\}.$$

Equation (36) can be simplified further by choosing $\varepsilon_1 = \varepsilon_0$. The series summation terms in equation (36) all vanish because $\alpha = 0$ in this case. This simplified result is identical to that presented in [22], in which the result is derived in the spatial domain directly.

3. Numerical Implementation

3.1 Calculation Method

In order to calculate the sensor transcapacitance, $C_T$, the method of moments (MoM) [23] is utilized in the numerical calculations. In the following calculation examples, all the sensors share the configuration shown in FIG. 1, where the central disc is charged to the potential $V_1 = 1$ V and potential of the outer ring is kept at $V_2 = 0$ V.

Figure 4:
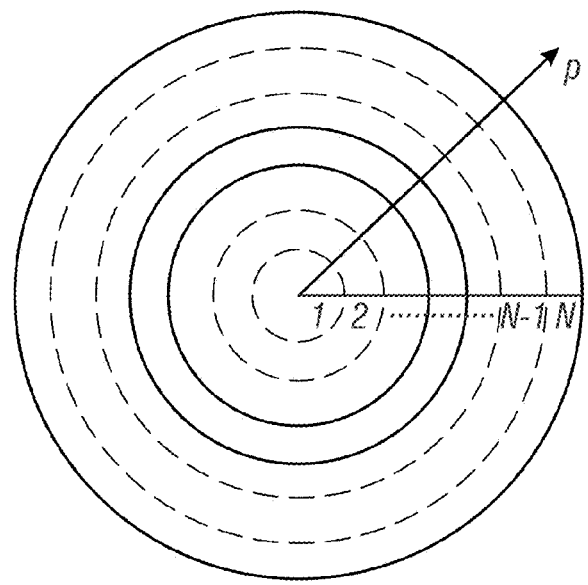
FIG. 4 illustrates a concentric sensor divided into N circular filaments, each with a constant surface charge density that is constant with respect to variation in $\rho$

The electrostatic potentials due to a point source, derived above, serve as the Green's functions in the MoM simulations. As shown in FIG. 4, the concentric electrodes of the sensor are divided into N circular filaments each with width $\Delta$ and a surface charge density that is constant with respect to variation in $\rho$. For the test-piece structure shown in FIG. 2, the potential at a given observation point $(\rho, \phi, 0)$ due to a source point $(\rho', \phi', 0)$ can be expressed as follows, by slightly modifying equations (26) to (30):

$$\Psi(\rho, \phi, 0 \mid \rho', \phi', 0) = \quad (37)$$

$$\frac{1}{2\pi(\varepsilon_0 + \varepsilon_1)} \times \left\{ \frac{1}{|r - r'|} - (1+\alpha) \left[ \begin{array}{c} G_1(|\rho - \rho'|) + G_2(|\rho - \rho'|) + \\ G_3(|\rho - \rho'|) + G_4(|\rho - \rho'|) \end{array} \right] \right\}$$

where $$|r - r'| = \sqrt{\rho^2 + \rho'^2 - 2\rho\rho' \cos(\phi - \phi')}, \quad (38)$$

$$G_1(|\rho - \rho'|) = \sum_{n=0}^{\infty} \sum_{l=0}^{\infty} \sum_{m=0}^{\infty} (-1)^n K_{mn}(\alpha, \beta) \quad (39)$$

$$K_{ln}(\delta, \gamma) \times \frac{\delta}{\sqrt{|r - r'|^2 + [2(mT_1 + nT_2 + lT_3 + h_3)]^2}}$$

and $G_2(|\rho - \rho'|)$, $G_3(|\rho - \rho'|)$, and $G_4(|\rho - \rho'|)$ can be modified similarly. For other test-piece configurations, the appropriate Green's function should be used. Moreover, the potential at such an observation point due to points on a charged sensor shown in FIG. 1 can be derived by integrating equation (37) over the sensor electrode surface:

$$\Psi(\rho, 0 \mid \rho', 0) = \frac{1}{2\pi(\varepsilon_0 + \varepsilon_1)} \times \int_{disc+ring} K(\rho, 0 \mid \rho', 0) \sigma(\rho') \rho' d\rho', \quad (40)$$

where $\sigma(\rho')$ is the sensor surface charge density and $$K(\rho, 0 \mid \rho', 0) = \int_0^{2\pi} \left[ \frac{1}{|r - r'|} - (1+\alpha) \sum_{i=1}^{4} G_i(|\rho - \rho'|) \right] d\phi'. \quad (41)$$

One thing to notice is that because of the cylindrical symmetry of the sensor structure, the resulting potential in space is independent of the azimuthal angle $\phi$. Therefore, the problem of calculating the sensor surface charge distribution, which is determined by the potential distribution, is reduced to the $\rho$-direction only. For observation points on the sensor electrodes, the boundary conditions for the potential can be expressed as $$\Psi_i(\rho, z = 0) = \frac{1}{2\pi(\varepsilon_0 + \varepsilon_1)} \times \int_{disc+ring} K(\rho, 0 \mid \rho', 0) \sigma(\rho') \rho' d\rho' = V_m, \quad (42)$$

where points on the central disc are denoted by m=1 while those on the outer ring are denoted by m=2. In order to solve for the sensor surface charge distribution $\sigma(\rho')$ using MoM calculations, the following expansion is used:

$$\sigma(\rho') = \sum_{j=1}^{N} \sigma_j b_j(\rho') \quad (43)$$

where $b_j(\rho')$ is the basis function and $\sigma_j$ is the unknown coefficient. Here, we choose $b_j(\rho')$ as the following function for filaments on the inner disc $$b_j(\rho') = \begin{cases} \dfrac{1}{\sqrt{s^2 - (\rho')^2}}, & (j-1)\Delta < \rho' < j\Delta \\ 0, & \text{elsewhere,} \end{cases} \quad (44)$$

where s is the radius of the inner disc. For the filaments on the outer annular ring, $b_j(\rho')$ is chosen as $$b_j(\rho') = \begin{cases} \dfrac{1}{\sqrt{(s+g)^2 - (\rho')^2}} \times \dfrac{1}{\sqrt{(D/2)^2 - (\rho')^2}} & (j-1)\Delta < \rho' < j\Delta \\ 0, & \text{elsewhere,} \end{cases} \quad (45)$$

where g is the gap between the two sensor electrodes and D is the diameter of the sensor. This form of basis function has the advantage of modeling the edge effect of the charge distribution discussed later. To resolve the N unknown $\sigma_j$ coefficients, it is then required that the boundary conditions for $V_m$ in equation (42) are satisfied for each circular filament on the sensor surface. To evaluate equation (42) in N different filaments, weighting (or testing) functions $w_i(\rho)$ are needed. Here, we choose the weighting and basis functions to be the same, known as Galerkin's method. For filaments on the inner disc, $$w_i(\rho) = \begin{cases} \dfrac{1}{\sqrt{s^2 - (\rho')^2}}, & (i-1)\Delta < \rho' < i\Delta \\ 0, & \text{elsewhere,} \end{cases} \quad (46)$$

while the weighting function for filaments on the outer annular ring $$w_i(\rho) = \begin{cases} \dfrac{1}{\sqrt{(s+g)^2 - (\rho')^2}} \times \dfrac{1}{\sqrt{(D/2)^2 - (\rho')^2}} & (i-1)\Delta < \rho' < i\Delta \\ 0, & \text{elsewhere,} \end{cases} \quad (47)$$

where i=1, 2, ..., N. Discretizing the integral equation using weighting functions in each of the N filaments, equation (42) turns into the following matrix equation:

$$\begin{bmatrix} G_{11} & G_{12} & \ldots & G_{1N} \\ G_{21} & G_{22} & \ldots & G_{2N} \\ \vdots & \vdots & \ddots & \vdots \\ G_{N1} & G_{N22} & \ldots & G_{NN} \end{bmatrix} \times \begin{bmatrix} \sigma_1 \\ \sigma_2 \\ \vdots \\ \sigma_N \end{bmatrix} = \overline{V} \quad (48)$$

where $$G_{ij} = \int_{i\Delta}^{(i-1)\Delta} w_i(\rho) \times \left[ \int_{j\Delta}^{(j-1)\Delta} K(\rho, 0 | \rho', 0) b_j(\rho') \rho' \, d\rho' \right] \rho \, d\rho. \quad (49)$$

For the $\underline{V}$ matrix, if the element is located on the central electrode, its value is $V_1=1$ V; while the values for those elements located on the outer ring are $V_2=0$.

From equation (48), the sensor surface charge distribution $\sigma(\rho')$ can be calculated. Once $\sigma(\rho')$ is known, one can integrate over the electrode surfaces and find the total charge on both inner and outer electrodes. The sensor output signal, which is the transcapacitance $C_T$ between those two electrodes, can be ultimately calculated through $$C_T = \dfrac{Q_{outer}}{V_{inner}} \bigg|_{V_{outer}=0} \quad (50)$$

where $Q_{outer}$ is the total charge on the outer electrode, while $V_{inner}$ and $V_{outer}$ respectively represent the voltage on the inner and outer electrodes. Choosing this convention leads to $C_T<0$, whereas $|C_T|$ is compared with experiment in the following.

3.2 Example Calculations

Figure 5:
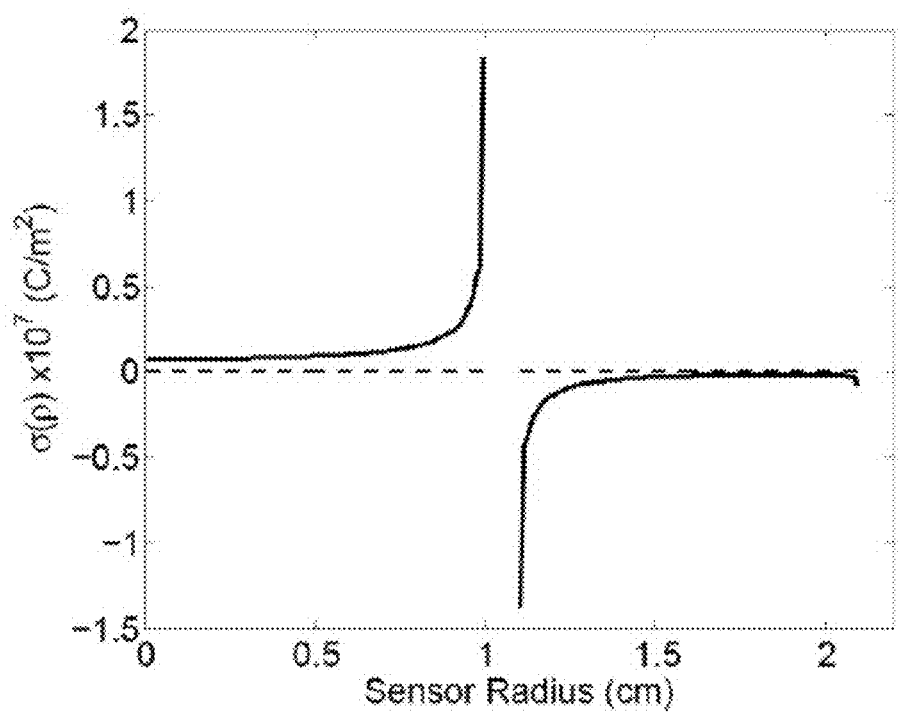
FIG. 5 illustrates a calculated surface charge distribution for the sensor shown in FIG. 1 in contact with a half-space dielectric. Sensor configuration: s=t=10 mm, g=1 mm, $V_{inner}$=1 V, and $V_{outer}$=0 V. The test-piece has relative dielectric constant $\epsilon_r$=8.

FIG. 5 shows an example of the sensor surface charge distribution, where the sensor is placed above a half-space dielectric with relative permittivity $\in_r=8$. The sensor configuration is s=t=10 mm and g=1 mm Due to the edge effect, the surface charge density at the edge of the inner charged electrode is singular. This positive charge distribution results in a negative surface charge distribution on the outer electrode. The surface charge density on the inner edge of the outer electrode tends to infinity much faster than that on the outer edge, because of its smaller radius and stronger interaction with the inner electrode. It is worth mentioning that when one applies a different combination of potentials on the inner and outer electrodes, the sensor surface charge distribution changes correspondingly. However, the sensor transcapacitance $|C_T|$, which is the intrinsic property of the sensor and only determined by its own structure, is unchanged. The sensor transcapacitance, $|C_T|=5.398$ pF for this case, is calculated through equation (50).

Figure 6:
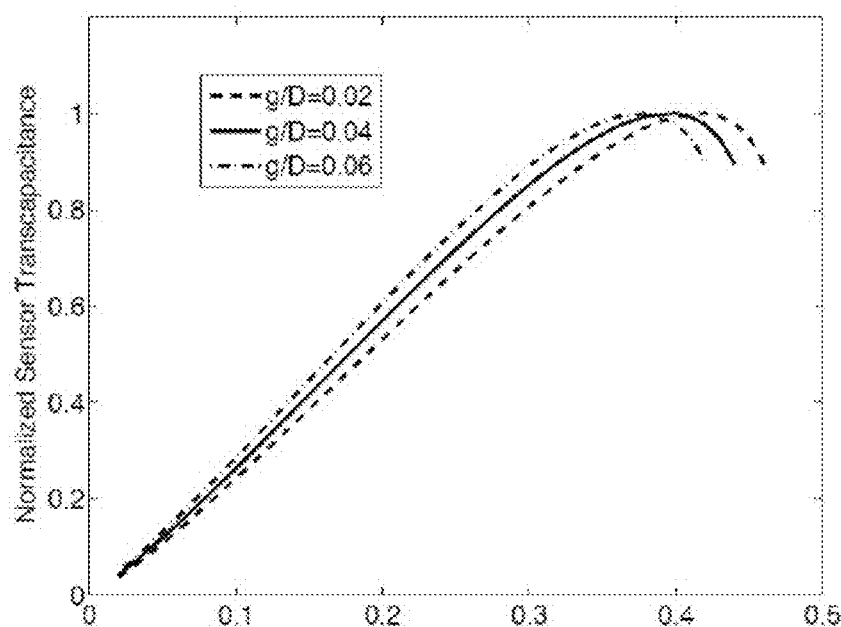
FIG. 6 is a graph illustrating a normalized sensor transcapacitance versus changing sensor disc radius s and electrode gap g. The sensor outer radius D/2=s+g+t is fixed.

Numerical calculations based on the same test-piece have been carried out to investigate the optimal sensor configuration giving the maximum output signal $|C_T|$. The sensor output signal as a function of s and g is plotted in FIG. 6. In the calculation, the sensor outer radius D/2=s+g+t is fixed and all the curves in FIG. 6 are normalized with respect to their own maximum values. As can be seen from the figure, for any given g, the sensor output signal increases to a maximum value and then decreases as s increases. This is because as s increases, the width of the outer electrode t decreases, resulting in stronger edge effects on its surface charge distribution. These stronger edge effects result in more charges accumulated on the outer ring, and therefore the sensor output signal is increased according to equation (48). In this regime, the surface charge density is the dominant factor determining the total surface charge $Q_{outer}$. However, as s increases and passes a certain value, the sensor output signal starts to decrease. This is due to the fact that the diminishing surface area of the outer electrode becomes dominant in determining the total surface charge $Q_{outer}$. As a result, we observe an optimal sensor configuration for a given g that gives the maximum $|C_T|$. It is also verified in our calculations that the shape of all the curves in FIG. 6 do not depend on the actual size of the sensor and the applied electrode voltage, but only on the relative values of s, g, and D. Similarly, as g increases, the interaction between the inner and outer electrodes is decreased, and the surface charge density at their neighboring edges diminishes accordingly. Because of the decreased edge effect and surface charge density, the outer electrode needs more surface area to achieve its maximum $Q_{outer}$, which is directly proportional to $|C_T|$. This is why as g/D increases, the s/D value that yields the maximum $|C_T|$ decreases in FIG. 6. As one can imagine, the absolute magnitude of $|C_T|$ also becomes smaller for larger g and fixed s and D values, due to the same reasoning mentioned above. Consequently, in order to achieve the maximum $|C_T|$, it is desirable to maintain high s/D and low g/D ratios. Nevertheless, it is worth mentioning that the sensitive area of the sensor closely corresponds to the location of the gap between its two electrodes, and there will be an insensitive zone at the center of those sensors with relatively large s values.

Figure 7:
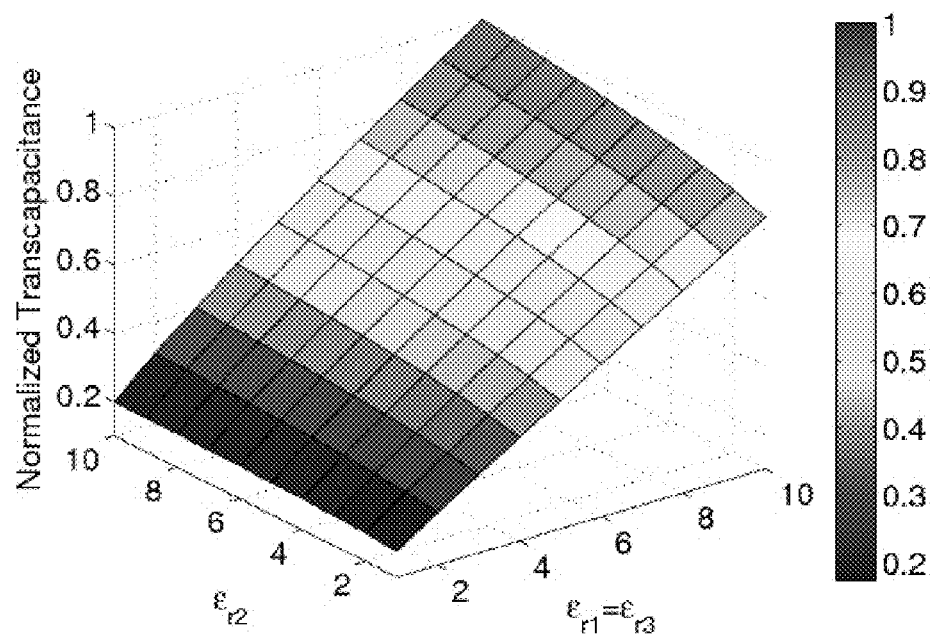
FIG. 7 illustrates how a calculated sensor output signal $|C_T|$ changes as a function of $\epsilon_{r1}$=$\epsilon_{r3}$ and the core-layer relative permittivity $\epsilon_{r2}$. $|C_T|$ is normalized by its own maximum value for this calculation, which is 4.66 pF. Sensor configuration is as for FIG. 5.

Another example, addressing sensor sensitivity to changes in core permittivity of a three-layer structure, is presented here. We are interested in this problem because one potential application of the sensor is detection of ingressed water or inhomogeneities in the core of an aircraft radome structure, which is typically a three-layer sandwich structure. In the numerical calculation, the infinite series summations in equations (27) to (30) are truncated to N=10 terms each. The difference between N=10 and N=100 terms is only 0.008% while the latter is extremely time-consuming. The sensor configuration is s=t=10 mm and g=0.5 mm. The test-piece is shown in FIG. 2, where $T_1=T_3=24$ mm, $T_2=3$ mm, and medium 4 is replaced by free space. The relative permittivity of the top and bottom layers, $\epsilon_1$ and $\epsilon_3$, is chosen to be the same. These parameters are also adopted in later benchmark experiments described in Section 4. FIG. 7 shows how the normalized sensor output signal $|C_T|$ changes as a function of $\epsilon_1=\epsilon_3$ and of the core relative permittivity $\epsilon_2$. In FIG. 7, $\epsilon_{r1}=\epsilon_{r2}=\epsilon_{r3}=1$ gives the limiting case of the sensor in free space; $\epsilon_{r1}=\epsilon_{r2}=\epsilon_{r3}\neq 1$ gives the case of the sensor on top of a one-layer test-piece in free space; and $\epsilon_{r1}=\epsilon_{r3}=1\neq\epsilon_{r2}$ gives the case of lift-off measurement of a one-layer test-piece in free space. It is seen from FIG. 7 that the slope of the curve representing the normalized $|C_T|$ as a result of changing $\epsilon_{r1}=\epsilon_{r3}$ when $\epsilon_{r2}=10$ is much greater than that obtained as a result of changing $\epsilon_{r2}$ when $\epsilon_{r1}=\epsilon_{r3}=10$ as expected due to the shielding effect of the top layer. In addition, high $\epsilon_{r1}=\epsilon_{r3}$ values give less sensitivity to $\epsilon_{r2}$ changes. This can be made more explicit by defining the percentage difference in the sensor output signal as follows:

$$\% \text{ difference} = P = \frac{|C_T|_{\epsilon_{r2}+\Delta\epsilon_{r2}} - |C_T|_{\epsilon_{r2}}}{|C_T|_{\epsilon_{r2}}} \times 100\%. \tag{51}$$

When $\epsilon_{r1}=\epsilon_{r3}=3$, $\epsilon_{r2}=2$, and $\Delta\epsilon_{r2}=1$, for example, then P is 3.66%. However, for the same $\epsilon_{r2}$ and $\Delta\epsilon_{r2}$, when $\epsilon_{r1}=\epsilon_{r3}=10$, P is only 2.99%. This percentage change in $|C_T|$ is expected to be even smaller when $\epsilon_{r1}$ becomes larger, which is reasonable because higher density electric fields are confined in the high $\epsilon_{r1}$ material. To improve sensor sensitivity to the permittivity change in the core-layer then, one can increase the gap g between the electrodes to some extent. For example, when g=1 mm rather than 0.5 mm as in the calculations of FIG. 7, and keeping all the other parameters the same, P is 3.62% when $\epsilon_{r1}=\epsilon_{r3}=3$ and 4.42% when $\epsilon_{r1}=\epsilon_{r3}=10$. However, the magnitude of the sensor output signal is decreased as g increases. Therefore, a trade-off between high sensor sensitivity and strong output signal is needed when determining the optimal sensor configuration for measurements detecting permittivity change in the core layer.

4. Experiments

4.1 Benchmark Experiments

In order to verify the validity of the theory developed above, benchmark experiments were carried out for one-, two, and three-layer dielectric test-pieces in free space, respectively. An Agilent E4980A precision LCR meter (20 Hz to 2 MHz) was utilized for the capacitance measurements. The operating frequency of the LCR meter was set to be 1 MHz. This particular frequency ensured that the measurement error of the LCR meter was less than 0.3% for a 1 pF capacitance, while at the same time giving a good approximation for the electrostatic case in the numerical model. A Novocontrol Alpha Dielectric Spectrometer was used to independently measure the dielectric constants of the samples used in the benchmark experiments. In the Novocontrol measurements, two 40-mm-diameter electrodes were used and the edge effect compensation was turned on, due to the fact that the thicknesses of the test-pieces were relatively large compared to the test fixture's electrode diameter. In addition, the test-piece thicknesses were measured by a digital thickness indicator with accuracy ±1 μm. These independently-measured test-piece thickness and dielectric constant values were used as the inputs of the calculation model.

Seven copper sensors of the configuration shown in FIG. 1 were fabricated by photolithography. Four sensors have g=0.5 mm and three have g=1 mm, with different s=t values. These sensors were deposited onto a 25-μm-thick Kapton® film to support the copper. By comparing the calculation result of a capacitive sensor (s=t=10 mm and g=0.5 mm) on top of a half-space dielectric ($\epsilon_r=8$) and that of the same sensor on top of a 25-μm-thick Kapton® film over the same half-space, it was estimated that the presence of the Kapton® film influences the measurement signal by less than 0.5%. For each of the following benchmark measurements, the test-piece was supported by three acrylic stands 50 cm above a wood-top working table to approximate the infinite test-piece in free space assumption in the calculation model. Tape was used to attach each sensor tightly against the test-piece to ensure minimum air gap between the sensor and the test-piece, due to the fact that the presence of an air gap can affect measurement results significantly. The tape was attached on the edges of the Kapton® film, far away from the sensor outer electrode. $|C_T|$ was measured by placing the probe of the Agilent probe test fixture 16095A across the two sensor electrodes. This probe test fixture was connected to the LCR meter and the capacitance values were read from the LCR screen.

Figure 8:
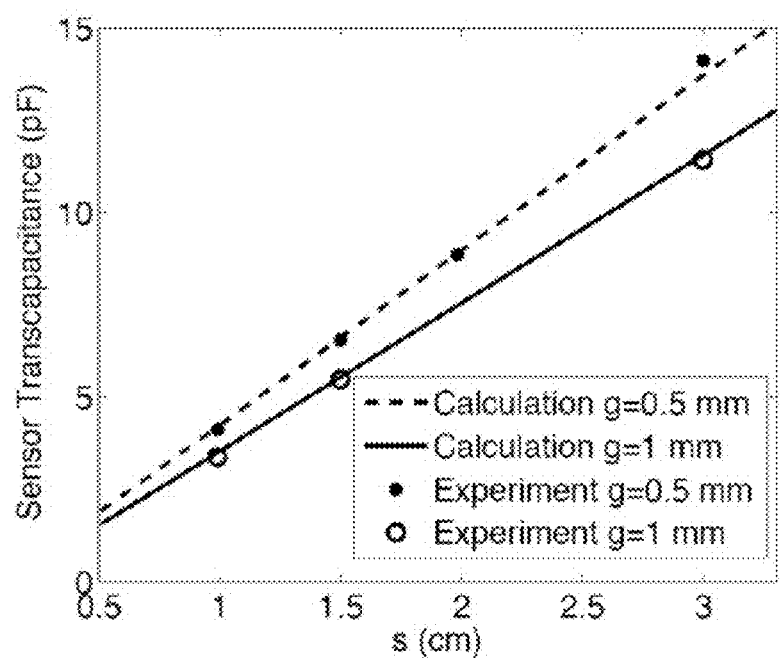
FIG. 8 illustrates measured and calculated $|C_T|$ for various sensor configurations (see FIG. 1) in contact with a glass plate with $\epsilon_r$=5.62 and thickness 3.02 mm.

To verify the results for the case of the capacitive sensor on top of a one-layer dielectric test-piece in free space, a glass plate with dimensions 305×305 mm² and thickness 3.02±0.01 mm was used. The test-piece dielectric constant was independently measured as 5.62±0.05. FIG. 8 gives the comparison between the numerical and experimental results. Experimental data show excellent agreement with the numerical results, to within 4%. Ten measurements were made for each sensor and the results were averaged. The maximum standard deviation in the measurements was found to be 2%. As can be seen, $|C_T|$ increases as s increases and decreases as g increases. Meanwhile, sensors with smaller s values show relatively greater standard deviation in the measured data. This is reasonable because when the scale of the sensor becomes smaller, the output capacitance is consequently smaller, and the noise from the surroundings in the measurement environment can have a relatively greater impact on the measurement results.

Figure 9:
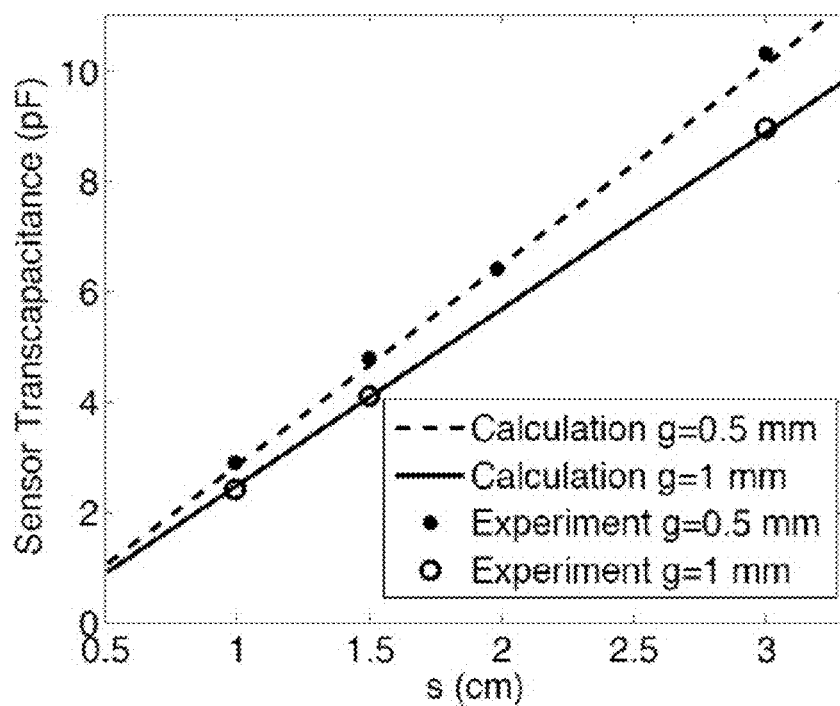
FIG. 9 illustrates measured and calculated $|C_T|$ for various sensor configurations (see FIG. 1) in contact with an acrylic plate, $\epsilon_r$=2.85 and thickness 2.39 mm, on top of a glass plate with parameters as for FIG. 8.
Figure 10:
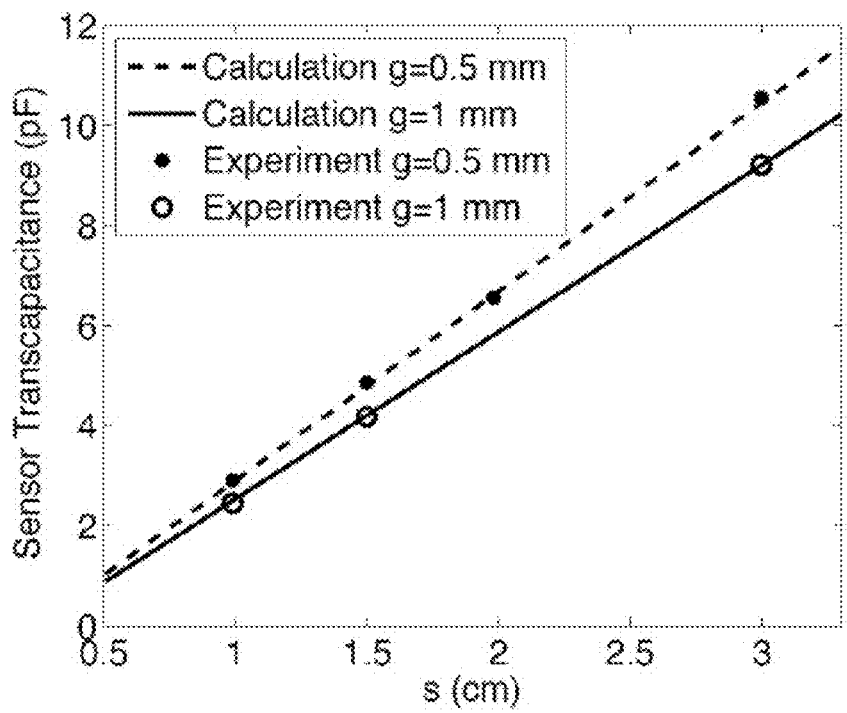
FIG. 10 illustrates measured and calculated $|C_T|$ for various sensor configurations (see FIG. 1) in contact with a three-layer acrylic-glass-acrylic structure. Layer parameters are as for FIGS. 8 and 9.

The case of the capacitive sensor on top of a two-layer dielectric test-piece in free space was verified by placing a 305×305 mm² acrylic plate with thickness 2.39±0.02 mm on top of the glass plate mentioned above. The independently measured acrylic dielectric constant was 2.85±0.05 in this case. Plastic clamps were used to make sure there was as little air gap as possible between these two plates. FIG. 9 gives the comparison between the numerical and experimental results. Again, very good agreement between experimental and theoretical results is observed. The maximum difference between the theory and experiment is less than 3% and the maximum standard deviation is 1% in these measurements. Similarly, FIG. 10 shows the comparison results for the case of the capacitive sensor on top of a three-layered acrylic-glass-acrylic structure. The top and bottom acrylic plates share the same parameters and the glass plate sandwiched in the middle is the same as that used previously. It is seen from FIG. 10 that, even for this more complex test-piece, very good agreement between theoretical predictions and experimental results is obtained. In this case, the maximum difference between the theory and experiment is 3% and the maximum standard deviation is 1%.

In conclusion, benchmark experiments show very good agreement with theoretical predictions. The output signal for the three-layer acrylic-glass-acrylic structure is slightly greater than that of the two-layer acrylic-glass structure but smaller than that of the one-layer glass plate. Because glass has a higher permittivity than acrylic, the sensor output signal of the one-layer glass plate is greater than that of the two-layer acrylic-glass structure. For the three-layer acrylic-glass-acrylic structure, the electric fields are mostly shielded by the glass plate. Therefore, adding an acrylic plate beneath the glass plate does not result in a significant change in the sensor output signal.

4.2 Detection of a Localized Anomaly in a Three-Layer Structure

Water intrusion has been a persistent problem for composite structures on aircraft. The freezing and thawing of intruded water in radomes and honeycomb sandwich flight controls can lead to disbond and structural failures. For this reason, water ingression experiments based on a sandwich structure were conducted to demonstrate the sensor's capability of detecting water intrusion in radome structures. The sandwich panel used in the following water ingression tests, shown in FIG. 11, has a paper and resin honeycomb core covered with fiberglass skins and closely resembles a real radome structure. Table 1 gives the detailed properties of the sandwich panel.

Figure 11:
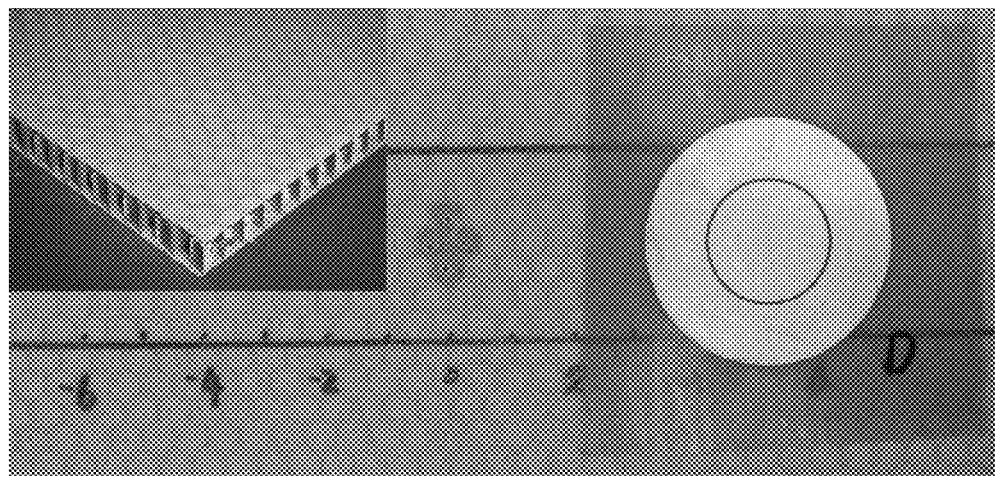
FIG. 11 illustrates a sensor on top of a 1 cc water-injected glassfiber-honeycomb-glassfiber sandwich panel. The sub-figure is a photograph of the sandwich panel whose properties are given in Table 1.
Figure 12:
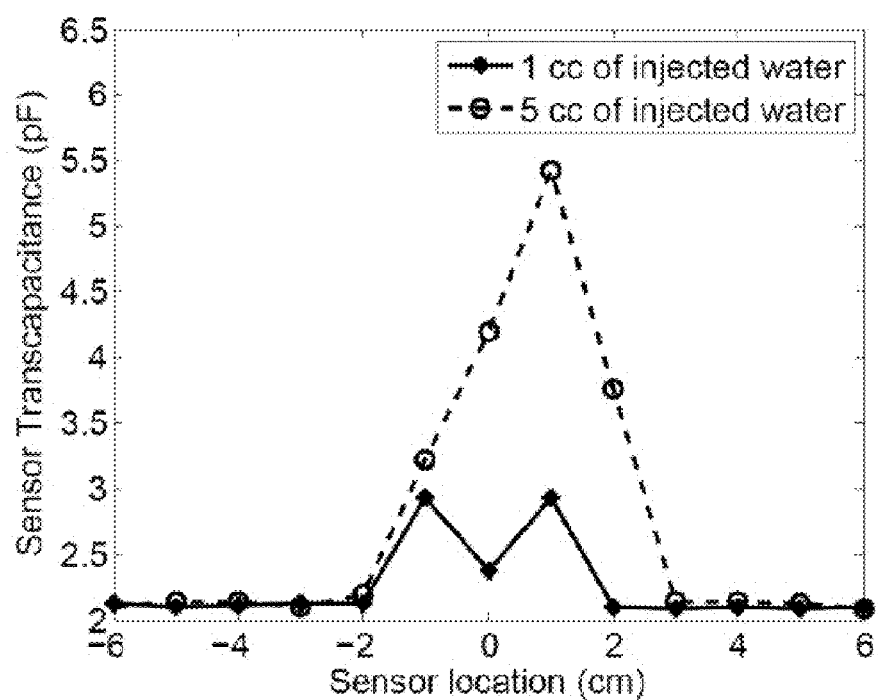
FIG. 12 illustrates measured $|C_T|$ for 1 cc of water injected into the glassfiber-honeycomb-glassfiber sandwich panel, FIG. 11. Sensor configuration is as for FIG. 5.

FIG. 11 shows the configuration for the coplanar capacitive sensor inspecting for 1 cc of injected water (4 honeycomb cells). The sensor scans from right to left on the test-piece surface, and the sensor output signal is read from the LCR meter screen. The solid line in FIG. 12 shows the sensor output signal for the configuration shown in FIG. 11. It is seen from the solid curve in FIG. 12 that there are two peaks and a valley between them in the output signal. This phenomenon arises from the fact that the most sensitive region of the sensor is at the gap between its two electrodes. As the sensor scans over the water, the left gap of the sensor meets the water-injected area first. This results in a peak in the sensor output signal. As the sensor continues to move to the left and reaches the place where it is centered over the water-injected area, there is a decrease in the sensor output signal, due to the fact that the water is off the sensor's most sensitive region. However, as the sensor continues moving, its right gap then meets the water-injected area. As a result, there is another peak in the sensor output signal. When the sensor moves away from the water-injected area, its output signal returns to the baseline signal for the unflawed panel.

In contrast, the dashed line in FIG. 12 shows the sensor output signal for 5 cc of injected water. In this case there is only one peak in the sensor output signal, and the magnitude of the peak is approximately double that measured for 1 cc of injected water. This is due to the fact that the water-injected area in this case is larger than in the previous case (20 honeycomb cells). As the sensor scans from the right to the left, its left gap reaches the water-injected area first. Correspondingly, there is an increase in the output signal. As the sensor keeps moving, its left gap still lies over the water injected area, while its right gap starts to come into the water injected area as well. This leads to the maximum sensor output signal shown in FIG. 12. However, as the sensor continues moving, its left gap leaves the water-injected area first and the sensor output signal starts to decrease. When both gaps move out of the water-injected region, the sensor output signal returns to the baseline signal for the unflawed panel.

5. Capacitive NDE System Using Sensor

Figure 13:
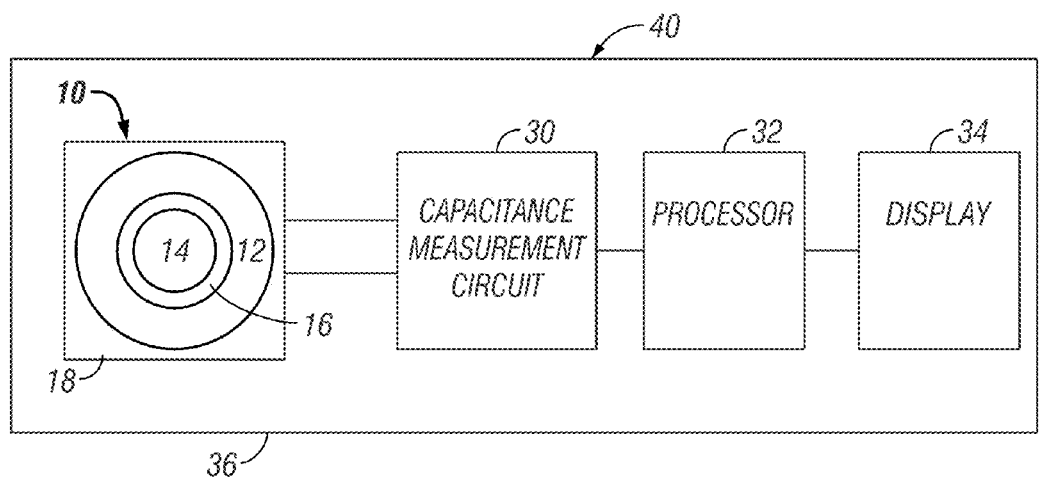
FIG. 13 is a block diagram illustrating one example of a capacitive NDE system which uses the sensor.

The present invention also provides for capacitive NDE systems which use the sensor. One example of such a system 40 is shown in FIG. 13. In FIG. 13, a concentric coplanar capacitive sensor 10 is shown having a charged central disc 14. There is an outer annular ring 12 which is coplanar with and outer to the charged central disc 14. In the embodiment shown, the rings 12, 14 are formed of copper and are placed on an insulative substrate, one example being a thin insulative film such as KAPTON® film. The sensor 10 is electrically connected to a capacitance measuring circuit 30. The capacitance measuring circuit is electrically connected to a processor 32 which may be operatively connected to a display 34. The system 40 may be housed in a housing 36 which may be handheld housing.

In operation, the system 40 uses the concentric coplanar capacitive sensor 10 to determine a transcapacitance between a first electrode formed by the charged central disc 14 and a second electrode formed by the outer annular ring 12. The transcapacitance may then be used by the processor 32 as input to one or more models for a material under test. The transcapacitance sensed may be interpreted by one or more models for various purposes such as to determine permittivity of individual layers in a multi-layered structure or to allow for water detection (including water detection in radome structures). The particular model used may depend upon the structure being tested and its properties as well as the particular NDE testing being performed.

Although a single probe system is shown, the present invention also contemplates the use of differential probes for optimal defect detection in the capacitive NDE system.

Therefore, a concentric coplanar capacitive sensor and related methods and systems have been disclosed. The present invention contemplates numerous options, variations, and alternatives. For example, the present invention contemplates variations in the materials used for the sensor, the specific size and geometry of the sensor, the type of structure being tested and the corresponding models for the structure under test, as well as other variations, options and alternatives.

6. Rotationally Invariant Hand-Held Capacitive Probe

A rotationally-invariant hand-held capacitive probe with concentric coplanar electrodes has been designed and built, FIG. 14, motivated by defect detection in aircraft radome sandwich structures. Two versions of the probe, with different target penetration depths, have been tested. The sensors have the same outer diameter (25.4 mm) but different gap width between the inner and outer electrodes. The probes were designed with the aid of the theoretical model previously discussed in which the capacitance is related to the electrode dimensions and the thickness and permittivity of each layer in a multi-layered dielectric test-piece. Experimental measurements of C with the probes in surface contact with one- and multi-layered dielectric test-pieces have been carried out and measured capacitance agrees with theoretical predictions to within 10%. The important parameters governing the penetration depth of this concentric capacitive sensor have been studied theoretically and experimentally by measurements on stepped Delrin® and HDPE slabs. Lift-off studies, both numerical and experimental, were carried out to investigate how lift-off affects measured C and the accuracy of the test-piece material properties when determined inversely from measured C. It is demonstrated that these hand-held probes are capable of detecting small embedded inhomogeneities in laminar structures, e.g., 1 cc of a low permittivity (low contrast) injected fluid in a glassfiber-honeycomb-glassfiber sandwich panel that gives rise to $\Delta C \sim 0.02$ pF is clearly detected. On the other hand, significant impact damage in glass fiber composites was not clearly detected. These capacitive probes are especially promising for discontinuity detection in sandwich structures.

6.1 Theoretical Background

Figure 14A:
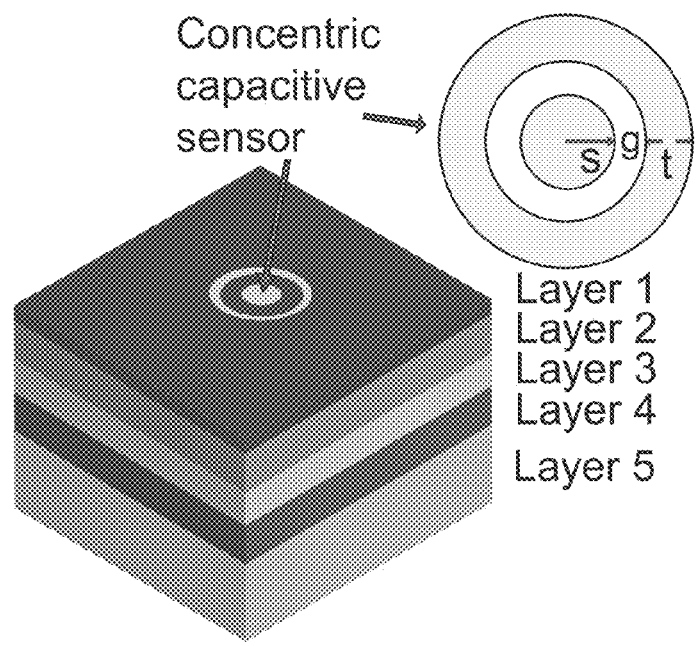
FIGS. 14A and 14B provide illustrations of concentric capacitive electrodes on top of a multi-layer dielectrics: (a) sensor configuration and test-piece structure used in the numerical modeling; (b) assembled hand-held probe based on the modeling in (a).
Figure 14B:
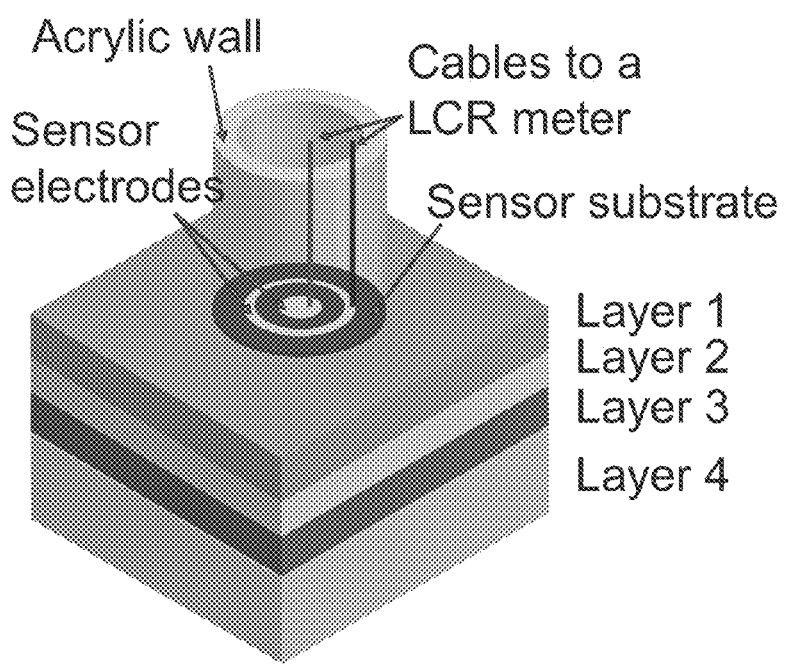

FIG. 14A depicts a concentric capacitive sensor in surface contact with a five-layer dielectric halfspace.

The capacitive sensor consists of an inner disc, radius s, and an outer annular ring, width t. The gap between these two electrodes is denoted g. A numerical model previously described provides a quantitative relationship between the sensor output signal, which can be measured, and the permittivity and thickness of each layer in the dielectric. In the model, the concentric sensor is considered to be infinitesimally thin while the test-piece is assumed to be laterally infinite. These assumptions are reasonable for electrodes that are relatively thin compared with the thickness of individual layers in the test-piece, and if the sensor is placed sufficiently far from the edges of the testpiece so that edge effects are negligible. In the theoretical model, the total charge Q on each sensor electrode is obtained from the calculated surface charge density and the sensor output capacitance computed from $C=Q/V$, where V is the potential difference between the two electrodes. For details of the calculation.

6.2 Probe Assembly

Two sets of concentric electrodes with different target penetration depths were fabricated by selectively etching a 18-µm-thick copper cladding (14 mL standard) off a 25.4-µm-thick Kapton® film by photolithography (American Standard Circuits, Inc.). Both sets of electrodes have fixed outer diameter 25.4 mm (1 inch), which was selected as a workable dimension for a hand-held probe, but have different gaps and other dimensions as listed in Table 1. The characteristic capacitance listed in Table 1 is the calculated free-space capacitance for each sensor. The gap between the two electrodes and the width of the outer electrode are relatively small values and strongly affect the sensor output capacitance. In order to measure these values very accurately, a Nikon EPIPHOT 200 microscope was used that is capable of achieving precision of +5 µm for good calibration and 50× magnification. The sensor inner electrode radius was measured using the "traveling microscope" method with accuracy +0.01 mm, due to its relative large dimension. It was found that the fabricated dimensions are the same as the nominal values under such measurement accuracy.

TABLE 1

Dimensions and calculated free-space capacitance for sensors A and B.

| | Inner electrode radius s (mm) | Outer electrode width t (mm) | Gap between the electrodes g (mm) | Characteristic capacitance (pF) |
|---|---|---|---|---|
| Sensor A | 10.67 ± 0.01 | 1.52 ± 0.01 | 0.518 ± 0.009 | 1.40 |
| Sensor B | 9.66 ± 0.01 | 1.527 ± 0.008 | 1.51 ± 0.01 | 0.99 |

Figure 15A:
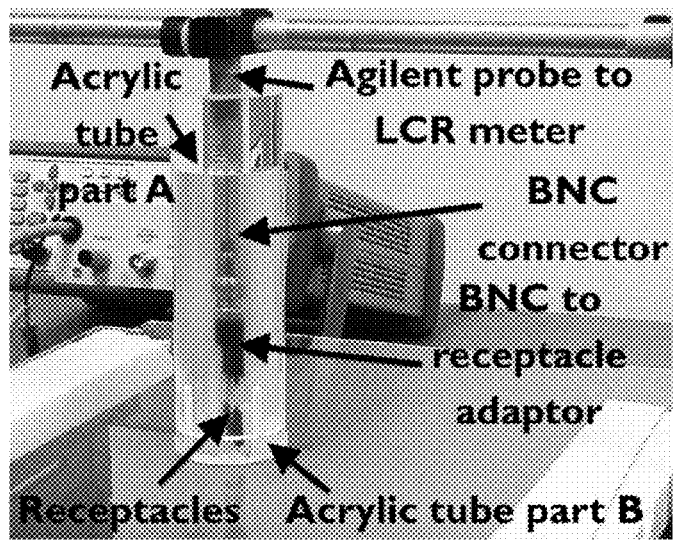
FIGS. 15A and 15B provide photograph of the assembled probe.
Figure 15B:
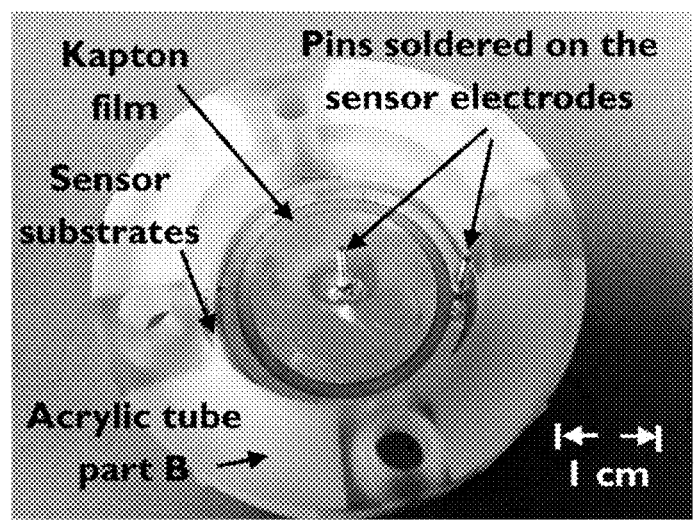
Figure 16:
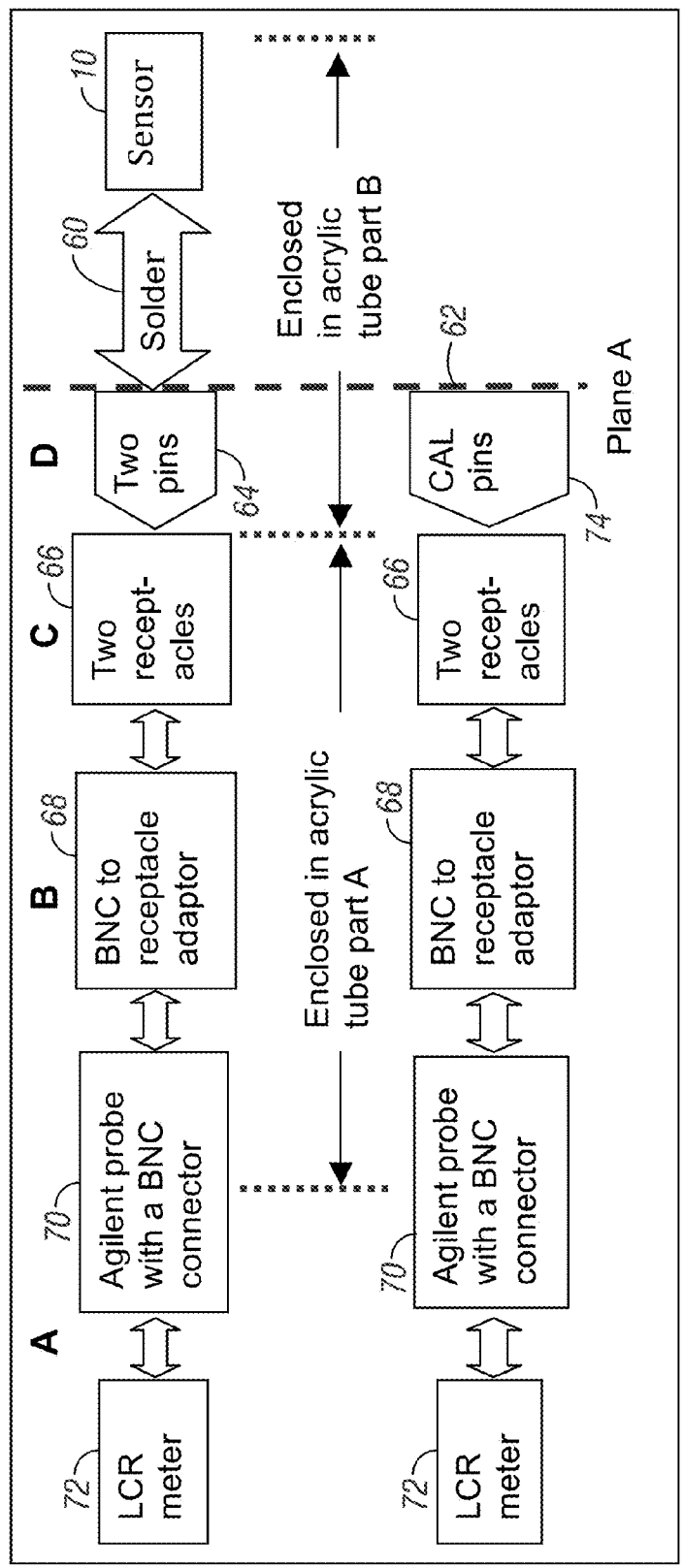
FIG. 16 is a block diagrams of the assembled hand-held probes illustrating equipment used in capacitance measurements and equipment used in probe calibration.

FIG. 15A shows the assembled capacitive probe, FIG. 15B shows the concentric electrodes, and FIG. 16 shows the components used to assemble the probe and components used in probe calibration. They consist of the following: a Rogers RO4003® dielectric sensor substrate with thickness 0.31±0.01 mm, on which concentric electrodes are supported; pins soldered to the electrodes; a BNC-to-receptacle adaptor that connects the pins to the BNC connector of an Agilent probe 16095A; and an Agilent LCR meter E4980A that displays the measured capacitance. The entire sensor structure is enclosed in a two-part acrylic tube. Assembled parts A and B are shown in FIG. 15A with part B shown in detail in FIG. 15B. The acrylic tube was divided into two to facilitate calibration of the probe, i.e., removal of effects of the probe structure on measured capacitance. The two parts, which can be easily attached or detached, were connected together using plastic countersunk screws.

6.3 Calibration Procedures

An effective calibration procedure removes the effect on the measured capacitance of all influences apart from the desired transcapacitance of the sensor. By comparing the probe measurement setup in FIG. 16 and the model used in numerical calculations (FIG. 14A), it can be seen that parasitic capacitances that affect measurement results include: A) that from the cable connecting the LCR meter 72 to the BNC connector on the Agilent probe 70, B) that from the BNC-to-receptacle adaptor 68, C) that from the two receptacles 66 in which the two soldered pins 64 on the sensor 10 are inserted, and D) that from the two pins 64 themselves. The goal is to calibrate the whole system and take into account all the parasitic capacitances up to the plane 62 shown in FIG. 16. In the LCR meter 72 measurement setup, the cable length option was set as 1 m. This setting automatically accounts for the parasitic capacitance due to the cable. In order to take into account parasitic capacitances from the BNC to receptacle adaptor 68 to the pins 64, open and short calibration steps are needed. Because the two pins 64 are soldered with sodder 60 to the electrodes, as shown in FIG. 16 two identical pins 62 were inserted into the ends of receptacles 66 during calibration. Open and short calibrations were then performed on plane 62 according to the procedures provided in the LCR meter manual. All parasitic capacitances up to plane 62 are accounted for after calibration. However, effective permittivity for the sensor substrate, as discussed below.

6.4 Experiments on Laminar Structures

As previously described, benchmark experiments measuring the transcapacitance of two concentric electrodes in contact with various large test-pieces showed agreement between experiment and theory of better than 4%. Similar experiments are performed here to assess the level of agreement between theory and experiment for the hand-held probes, which is expected to be poorer due to the hardware associated with the hand-held probe that is not modeled explicitly. In order to account for effects from part B of the acrylic tube, an effective permittivity for layer 1, FIG. 14A, was introduced. This effective permittivity was determined by placing the assembled probe in free space and measuring its capacitance. This measurement is considered in the numerical modeling as the case of a concentric capacitive sensor in surface contact with a one-layer dielectric (the sensor substrate) in free space. By assuming the thickness of layer 1 is the same as that of the sensor substrate and then varying its permittivity, a calculated probe output capacitance that agrees with the measured value to three significant figures was obtained. This permittivity value was subsequently assigned to be the effective permittivity of the sensor substrate with geometry shown in FIG. 14B. The effective sensor substrate permittivity for sensor A was determined to be 3.47 while that for sensor B was determined to be 3.31, at 1 MHz and room temperature. The effective permittivity values for both sensor configurations are greater than the substrate permittivity itself, 3.01±0.05, due to the existence of the acrylic tube part B (which has a relative permittivity of around 2.8). The effective permittivity of the sensor substrate for sensor A is greater than that for sensor B, because of the fact that sensor A has higher output capacitance values and influences from part B results in larger absolute changes in the capacitance for sensor A. Consequently, its effective substrate permittivity, which is inversely determined based on the output capacitance, is larger. These fitted sensor substrate effective permittivity values were subsequently used as inputs in the numerical model for the calculation of probe capacitances.

dielectric constant of the glass sheet was measured as 5.62±0.05 and that of acrylic was 2.85±0.05.

For all the measurements reported in this paper, the testpiece was supported 10 cm above a woodtop working table to approximate the free space assumption in the calculation model. The two probes with parameters listed in Table 1 were tested on five different laminar structures. The hand-held probes were pressed tightly against the test-piece surface to eliminate any air gap between the sensor substrate and the test-piece. As can be seen from Table 2, experimental results agree with calculated results to within an average of 7% for sensor A and 9% for sensor B. Notice that absolute differences in measured and calculated capacitance values for sensors A and B are similar in magnitude, and the greater relative differences observed for sensor B are due to the fact that its capacitance values are smaller.

The agreement between theory and experiment of within 10%, shown in Table 2, indicates that the structure of the probe give rise to some loss of quantitative accuracy, compared to the 4% agreement obtained in previous benchmark experiments for un-encased electrodes. Further, the calibration process here is not perfect. For example, the electrical contact condition between the receptacles and the two soldered pins is not identical to that between the receptacles and the calibration pins. In addition, the soldered joints on the electrodes are not accounted for in the calibration process.

6.5 Penetration Depth of Concentric Capacitive Sensors

In capacitive NDE, the penetration depth can be defined in terms of the sensor output capacitance [10, 14]. Consider a concentric capacitive sensor in surface contact with a one

TABLE 2

Measured and calculated capacitance of hand-held probes in surface contact with various test pieces.

| | Calculated C (pF) | | Measured C (pF) | | Relative Difference (%) | |
|---|---|---|---|---|---|---|
| | Sensor A | Sensor B | Sensor A | Sensor B | Sensor A | Sensor B |
| One-layer acrylic slab | 2.75 | 1.83 | 2.58 ± 0.01 | 1.69 ± 0.01 | −6.2 | −7.7 |
| One-layer glass slab | 3.57 | 2.53 | 3.26 ± 0.01 | 2.28 ± 0.01 | −8.7 | −9.9 |
| Two layer glass over acrylic structure | 2.93 | 2.03 | 2.73 ± 0.01 | 1.87 ± 0.01 | −6.8 | −7.9 |
| Two layer glass over acrylic-structure | 3.70 | 2.63 | 3.42 ± 0.01 | 2.37 ± 0.01 | −7.6 | −10.2 |
| Three layer acrylic-glass-acrylic structure | 2.93 | 2.03 | 2.73 ± 0.01 | 1.87 ± 0.01 | −6.8 | −7.9 |
| Average | | | | | −7.2 | −8.7 |

Relative differences are compared to the calculated capacitances. Uncertainty in measured C is 0.3%

Figure 17A:
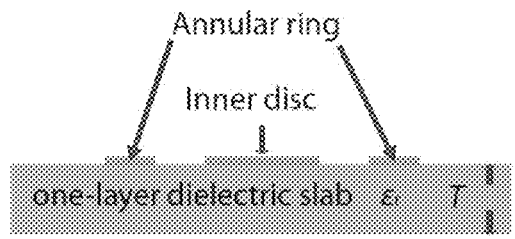
FIGS. 17A-17C penetration depth of concentric capacitive sensors.

Measurements reported in this paper were performed at room temperature. The LCR meter operating frequency was set at 1 MHz so that the measurement error from the LCR meter was less than 0.3% for a 1 pF capacitance. At the same time, 1 MHz is low enough to be a good approximation for the electrostatic assumption made in the numerical model. Samples used in the benchmark experiments are one-, two- and three-layer test-pieces formed by combinations of acrylic and glass plates with lateral dimensions 30 cm by 30 cm. A digital thickness indicator with ±1 μm accuracy was used to measure the plate thicknesses. The acrylic plates were 2.39±0.02 mm thick and the glass plate was 3.02±0.01 mm thick. A Novocontrol Alpha Dielectric Spectrometer was used to provide an independent value of the dielectric constants of the samples at 1 MHz, as inputs to the model. The layer dielectric slab with permittivity $\epsilon_r$ in free space (FIG. 17A). The penetration depth $D_{10}$ of a concentric coplanar capacitive sensor is here defined by identifying the one-layer test-piece thickness T or which the capacitance is 10% smaller than its value when in contact with a similar but infinitely thick test-piece. When this condition is satisfied, the sensor penetration depth value $D_{10}$ is equal to the testpiece thickness T and is dependent on the permittivity of the testpiece.

In other works, $D_3$ is defined as the penetration depth of capacitive sensors. Here we choose $D_{10}$ because the absolute difference in capacitance will be less than 0.1 pF if the capacitance is less than 3 pF and $D_3$ is adopted, and such small changes in capacitance are hard to measure especially when noise is present.

Figure 17B:
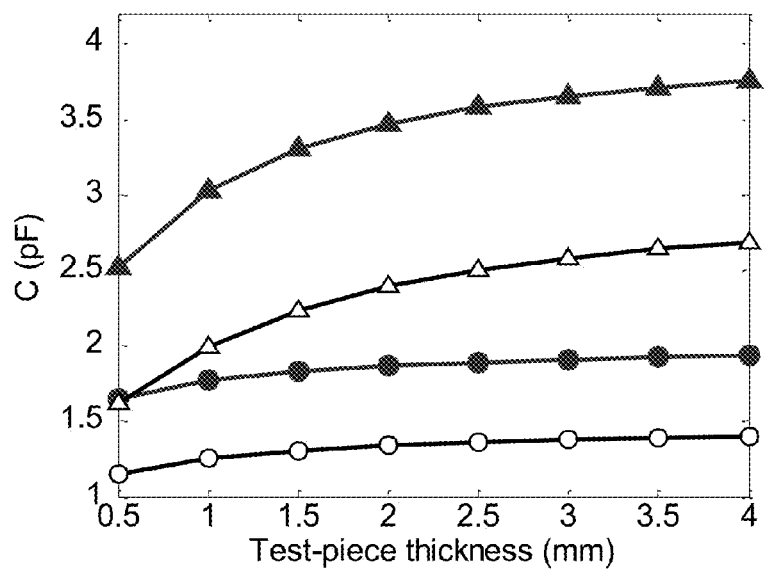
Figure 17C:
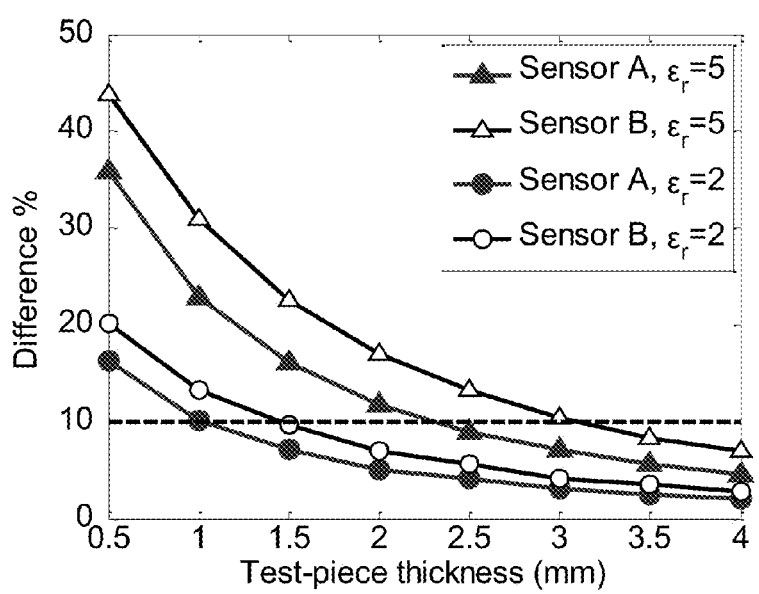

FIG. 17B shows the calculated sensor output capacitance as a function of the one-layer test-piece thickness and permittivity for sensors A and B and test-pieces with $\epsilon_r$=2 and 5. It can be seen that, for a given test-piece permittivity, the sensor capacitance increases as the test-piece thickness increases and asymptotically approaches a constant value as the thickness becomes large. Further insight about the sensor penetration depth is provided in FIG. 17C, in which the vertical axis is defined as $$\text{Difference \%} = \frac{|c - c_\infty|}{c_\infty} \times 100, \quad (52)$$

C is sensor capacitance for a particular test-piece slab and $C_\infty$ is that as the slab thickness tends to infinity. Notice that the sensor output capacitance approaches $C_\infty$ at different rates depending on sensor configuration and test-piece permittivity. For a given test-piece permittivity, sensor B always has larger penetration depth than sensor A, because of its wider inter-electrode spacing. This agrees with our intuition. It is also shown that, for a given sensor configuration, the sensor penetration depth is larger for test-pieces with higher $\epsilon_r$ values. Test-pieces with larger permittivity values must have larger thickness T in order to achieve a 10% difference in C for the slab with thickness T and a half space (see FIG. 17C), compared with test-pieces with smaller permittivity values.

Figure 18A:
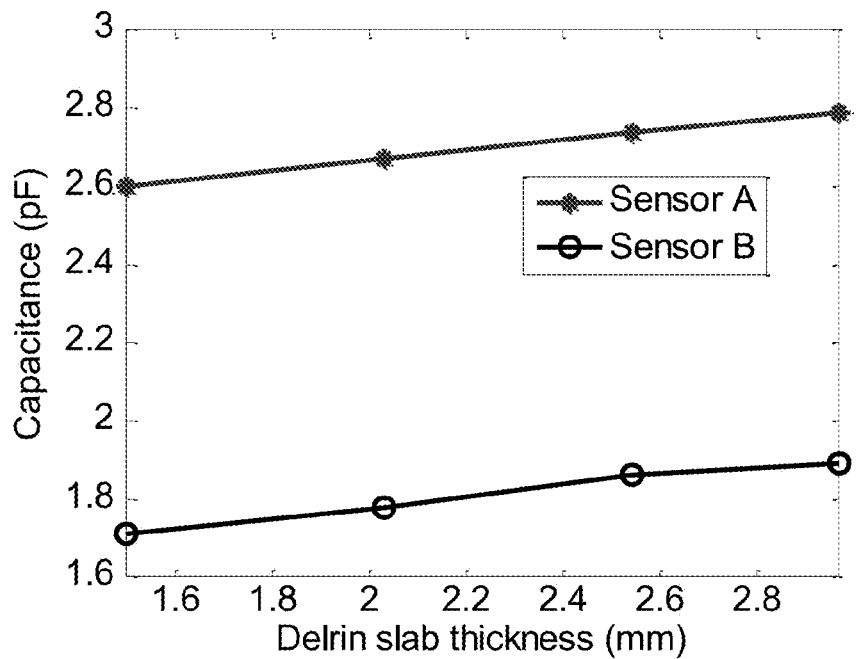
FIGS. 18A-18D illustrate measured capacitance of hand-held probes as a function of test-piece thickness.
Figure 18B:
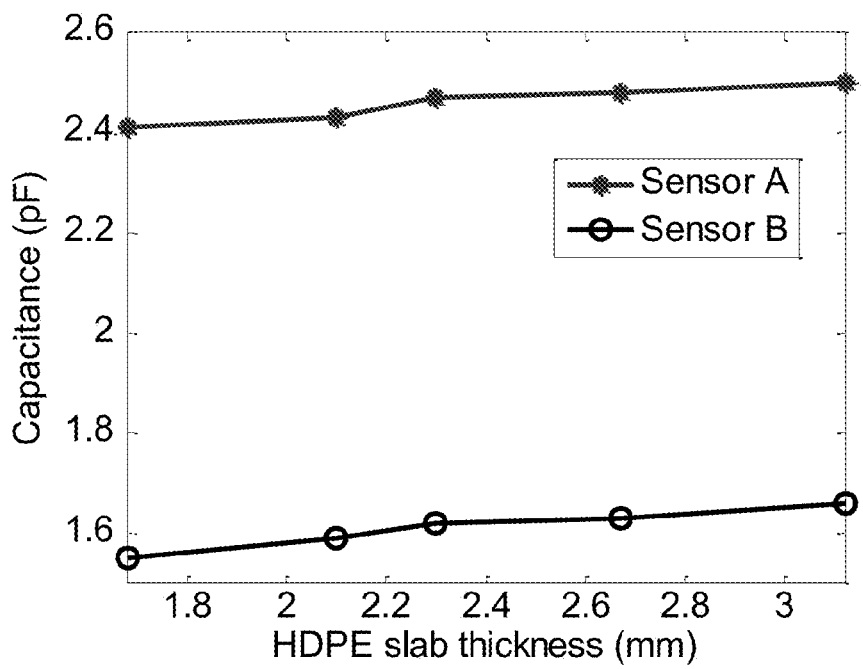
Figure 18C:
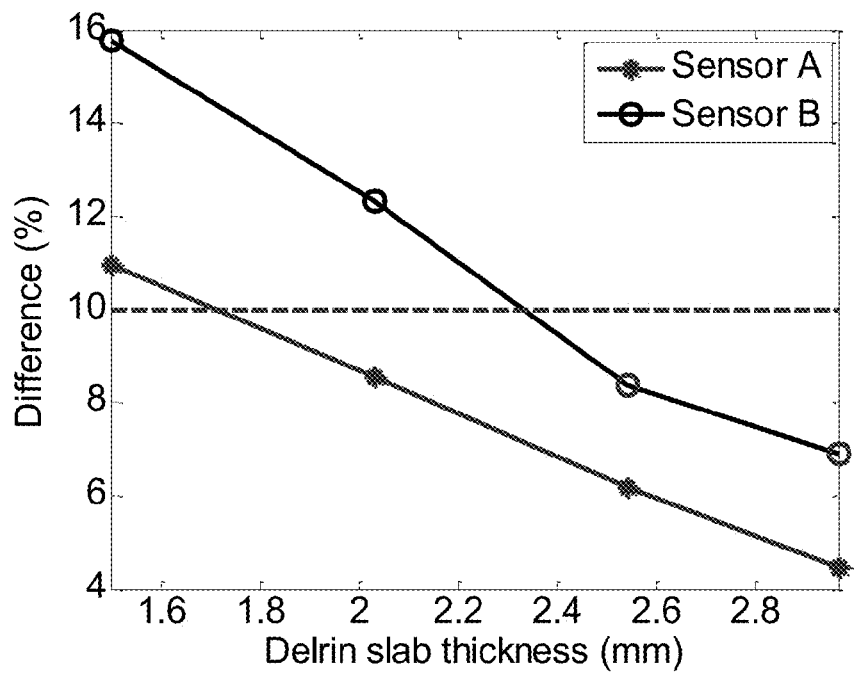
Figure 18D:
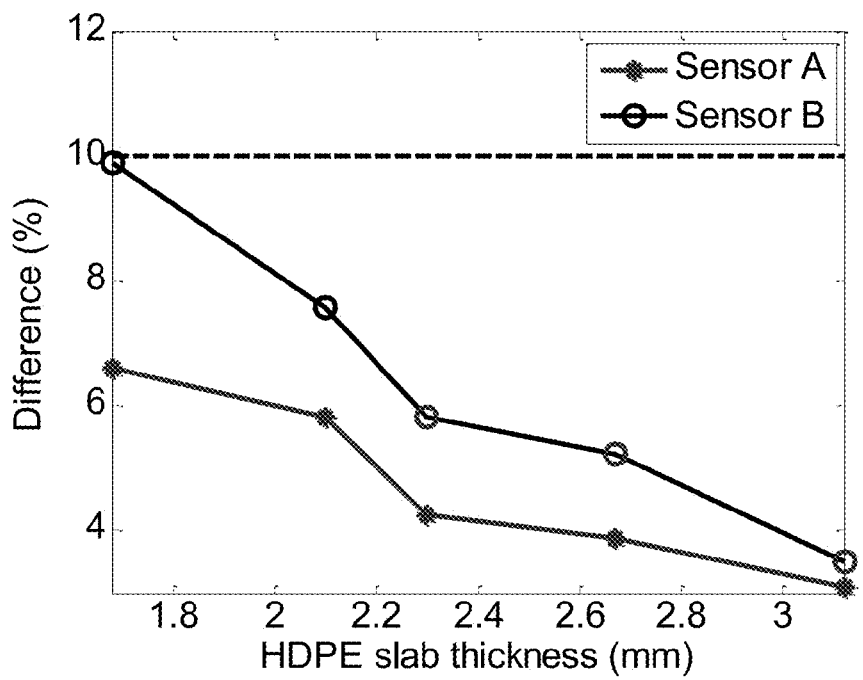
Figure 19A:
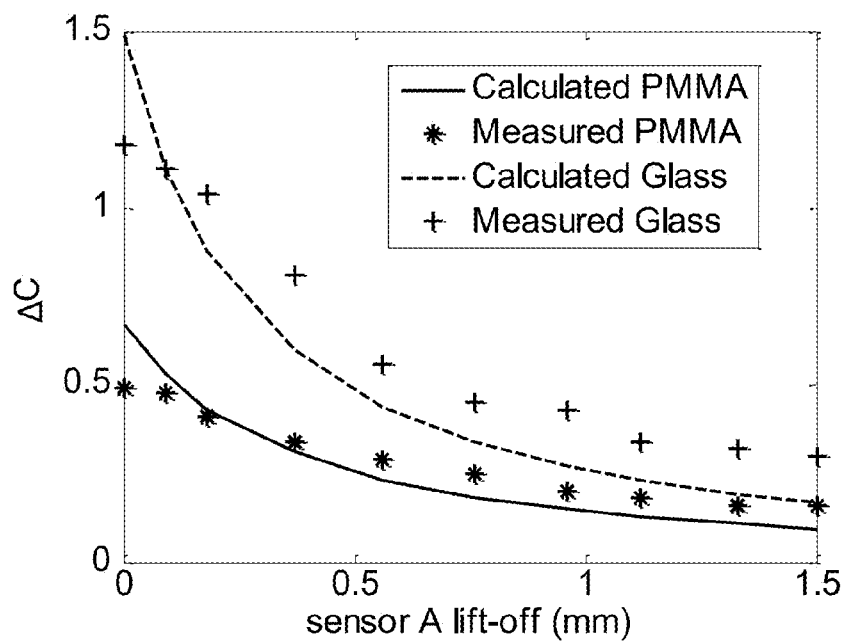
FIG. 19A is for sensor A.
Figure 19B:
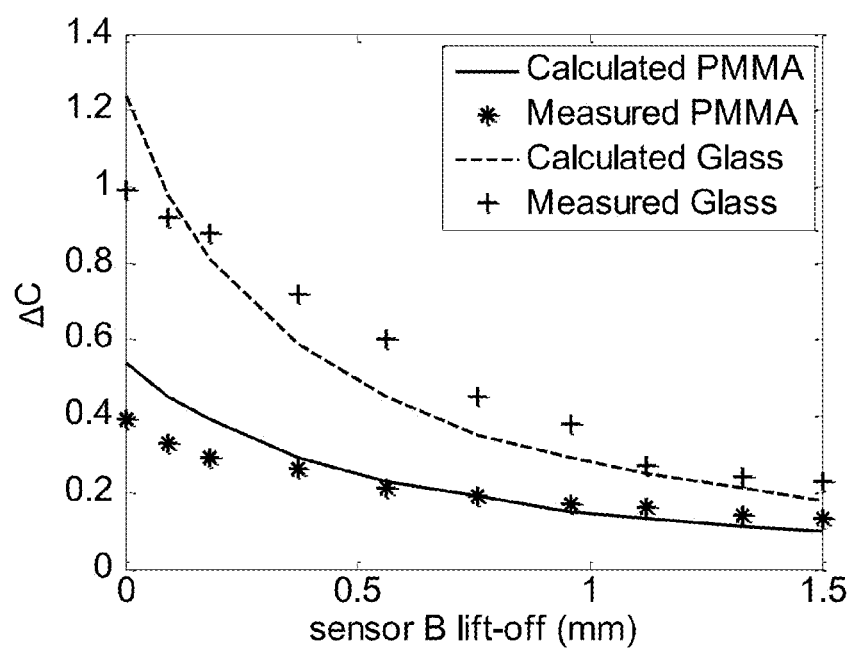
FIG. 19B is for sensor B.

FIGS. 18A and 18B show measured capacitance as a function of test-piece thickness, for both stepped Delrin® ($\epsilon_r$=3.82) and stepped HDPE ($\epsilon_r$=2.65) slabs. FIGS. 18C and 18D show relative differences between the capacitance measured values and that on the 18-mm-thick test-piece, which approximates a half-space. It can be seen that $D_{10}$ of both sensors is greater for the Delrin® slab than that for the HDPE slab in accordance with the predictions of FIG. 19B, and both sensors' sensitivity to test-piece thickness starts to decline as T increases. For a given test-piece, $D_{10}$ for sensor B is greater than for sensor A again in accordance with predictions of FIG. 17C). Additionally, good agreement (to within an average of 10%) between measured capacitances and numerical predictions is observed for test-pieces with permittivities and thicknesses in the range 2.65 to 3.82 and 1.50 mm to 3.12 mm, respectively.

In summary, for a given sensor configuration, sensor penetration depth increases as test-piece permittivity increases. For a given test-piece material, sensors with wider inter-electrode spacing have higher penetration depths but smaller output capacitances. Therefore, a trade-off exists between sensor output signal and penetration depth.

6.6 Capacitance as a Function of Probe Lift-Off

How do lift-off variations affect the measured probe capacitance and the accuracy of test-piece permittivity values that may be derived from those measurements? The experimental arrangement for measuring C as a function of lift-off from the test-piece is shown in FIG. 15A. The test-piece was adjusted to be horizontal using a level. The lift-off between the hand-held probe and the test-piece was precisely controlled by pressing the probe tightly against the test-piece with fixed-thickness plastic shims acting as spacers in between. These plastic shims were then removed carefully, without moving the test-piece or the hand-held probe. This procedure helps to ensure that the plane of the electrodes and the test-piece surface are in parallel, avoiding probe tilt. The thickness of the plastic shims was measured using a digital indicator and the resulting value considered to be the probe lift-off value.

The capacitance of the hand-held probes as a function of probe lift-off was measured, and compared with numerical predictions. In the numerical calculations, the probe substrate was again assigned the effective value derived from measurement of the free space probe capacitance, and layer 2 in FIG. 14A was assumed to be air with thickness equal to the lift-off value. The average difference between measured and calculated values was 7%. The difference $\Delta C = |C_{lift-off} - C_{air}|$ is plotted in FIGS. 19A and 19B for measurements on PMMA and glass slabs respectively, whose parameters are described earlier in the section discussing experiments on laminar structures. Clift-off corresponds to the capacitance.

Figure 19C:
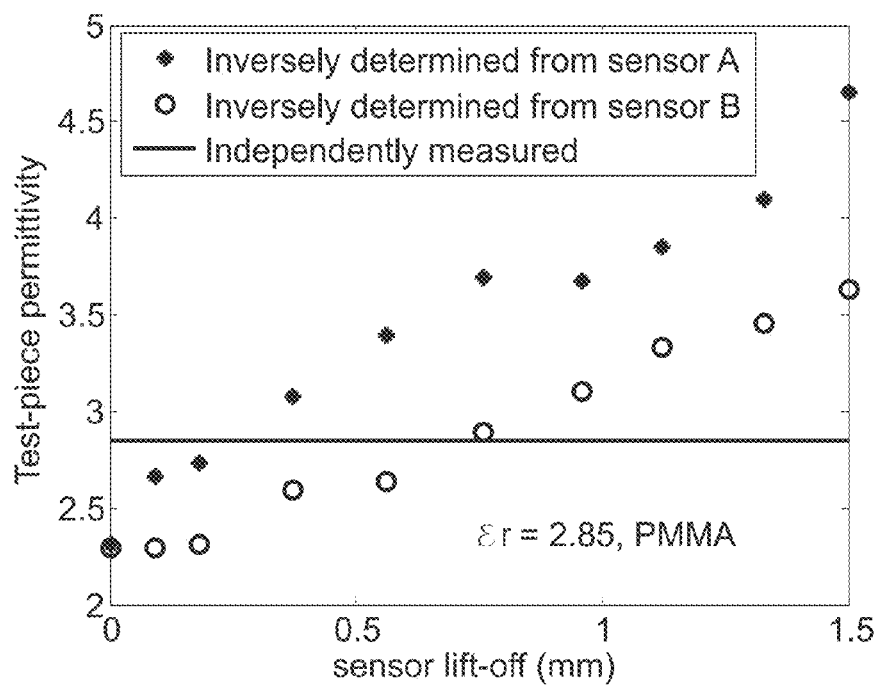
FIG. 19C and FIG. 19D illustrate permittivity determined for PMMA and glass, respectively.
Figure 19D:
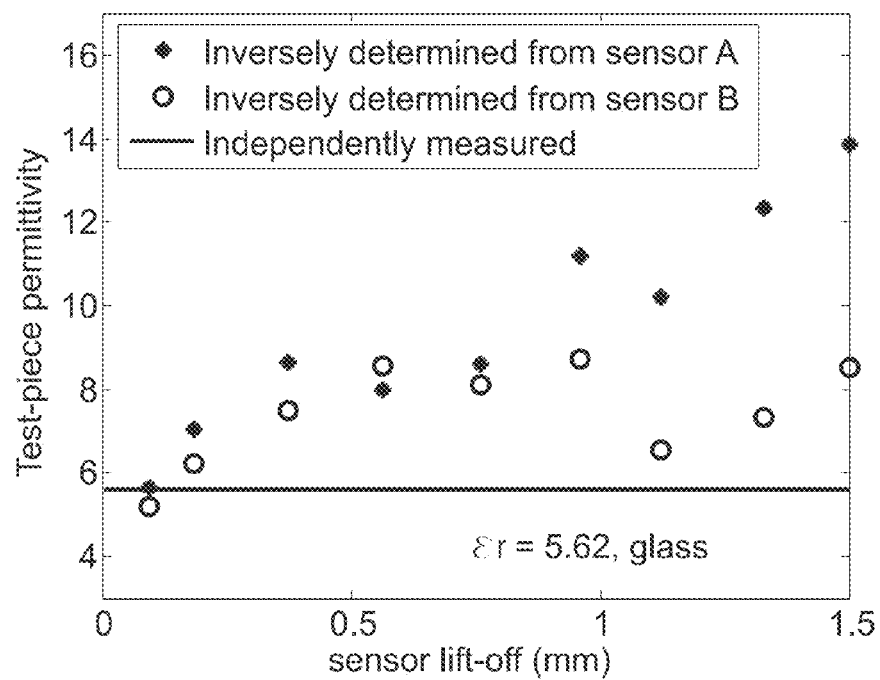

Test-piece permittivity values can be determined inversely from measured capacitance values using the model. The measured capacitances agree with the calculated ones the best when lift-off is large; since these situations are closest to the calibration environment of the probes. FIGS. 19C and 19D show the inversely determined permittivity values for the one-layered PMMA and glass, respectively. It is seen that when lift-off values are relatively small, the hand-held probes can characterize the test-piece material property fairly well. However, large lift-off values can result in inaccuracy in the inversely determined material permittivity information, even if the relative differences between the measured and calculated capacitances are small. This is due to the fact that the hand-held probes are most sensitive to the region near the sensor substrate. When the lift-off is large a slight difference in measured capacitance can result in a large difference in the inversely determined test-piece permittivity.

6.7 Detection of Embedded Inhomogeneities in Sandwich Structures

In some structures, such as radomes, it is important that the electrical properties do not vary in an uncontrolled way. Imperfect repairs or damage followed by ingress of water can give rise to inhomogeneities with electrical properties that contrast with their surroundings. Here we investigate the ability of the capacitive probes to resolve inhomogeneities of various size and permittivity embedded in a Delrin® plate and in the core of a glassfiber-honeycomb-glassfiber sandwich structure.

Two rows of holes of different diameters, 2.5, 5.0, 7.5, and 10 mm, were drilled in a 3.17-mm-thick Delrin® plate with permittivity $\epsilon_r$=4.14. One row of holes was left empty while the other was filled with Paraffin wax ($\epsilon_r$=2.1) to form zones with different permittivity contrasts. Table 3 lists the measured capacitances when the contrast zones are positioned directly beneath the sensor gaps. It is seen that both probes were able to detect the air-filled holes of all sizes, whereas both failed to detect the 2.5-mm-diameter wax filled holes, due to the lower permittivity contrast between Delrin® and wax (around 2) compared with that between Delrin® and air (around 4.1). On the other hand, because of its deeper penetration depth, sensor B was found more capable of detecting embedded zones than sensor A; see relative differences in Table 3.

Figure 20:
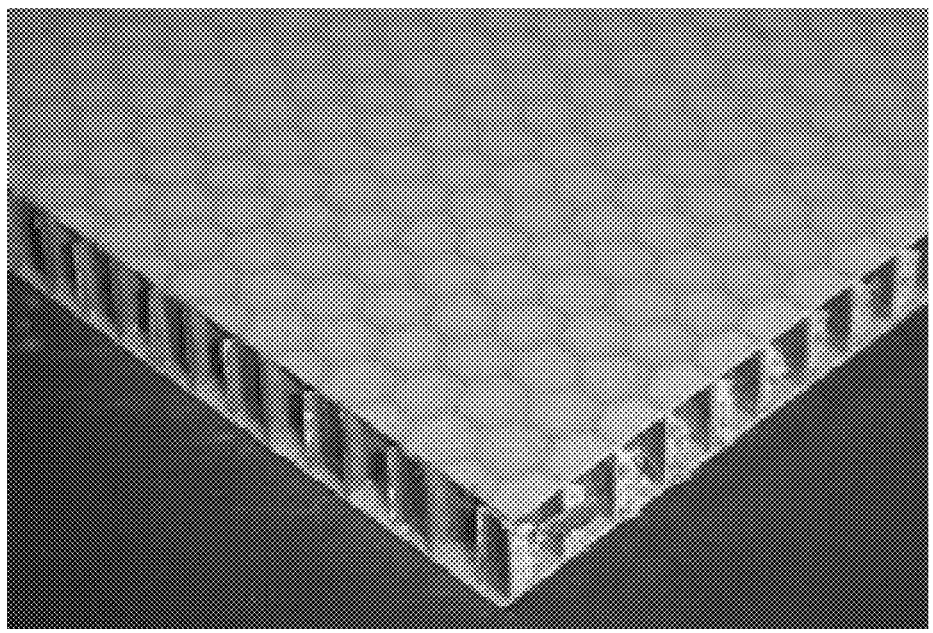
FIG. 20 is a photograph of the sandwich panel with parameters listed in Table 4.
Figure 21A:
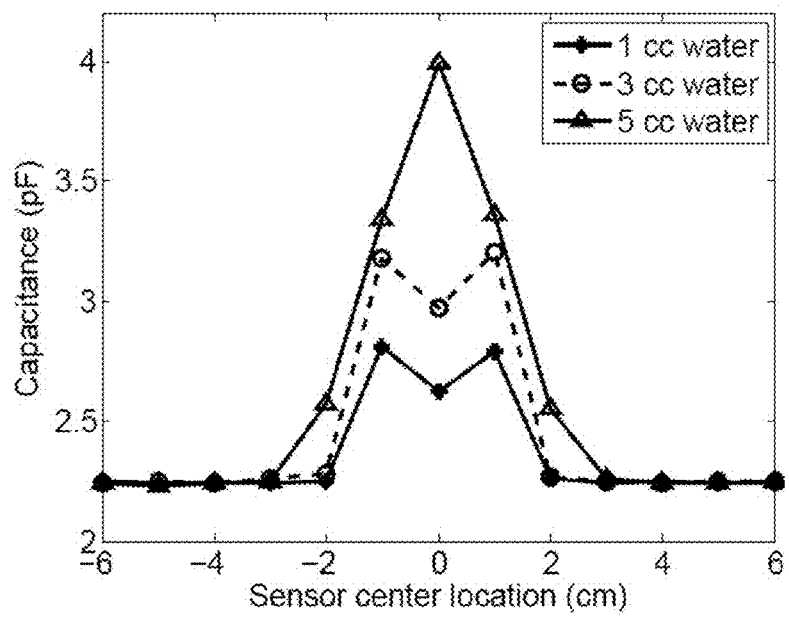
FIGS. 21A-21D illustrate capacitance measured as hand-held probes scan over glassfiber-honeycomb-glassfiber sandwich panels containing injected dielectric contrast agents water and olive oil.
Figure 21B:
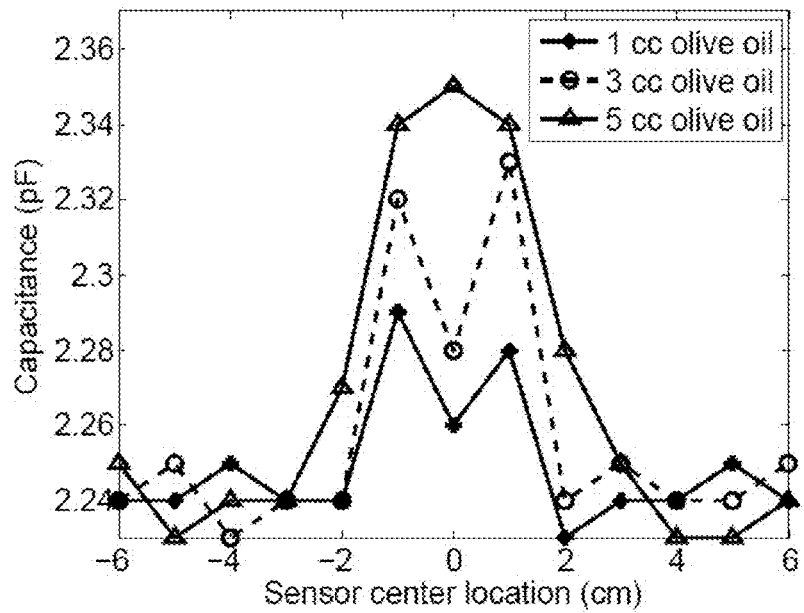
Figure 21C:
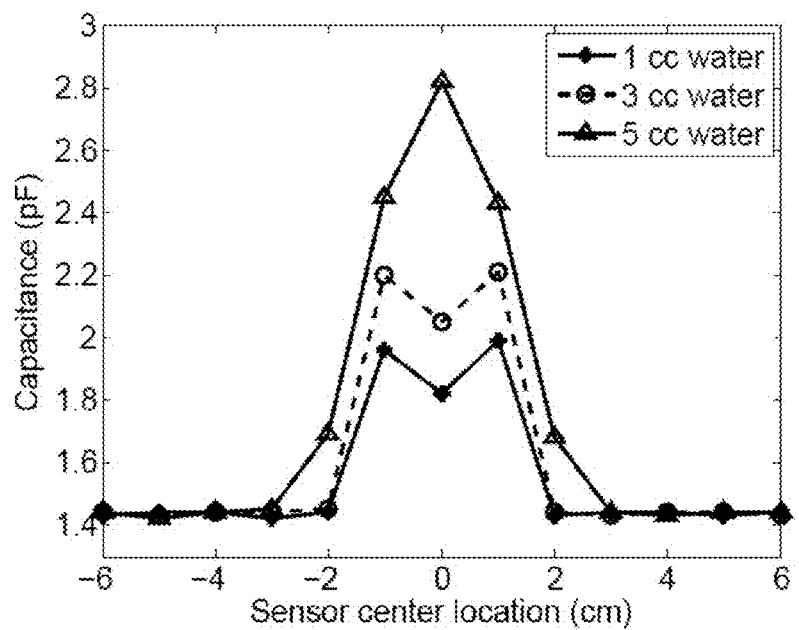
Figure 21D:
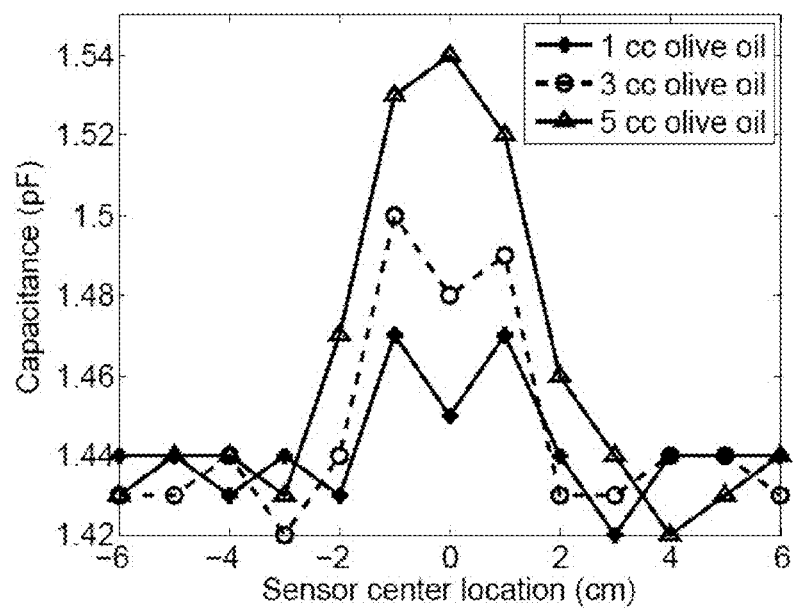

In order to investigate the effectiveness of the hand-held probes in detecting inhomogeneities in sandwich structures, different amounts (1, 3, and 5 cc) of water and olive oil ($\epsilon_r$≈8 and 3 at 1 MHz and room temperature, respectively) were injected into the honeycomb core of a glassfiber-honeycomb-glassfiber structure (FIG. 20). Parameters of the sandwich panel are listed in Table 4. 1 cc of injected liquid corresponds to 4 honeycomb cells with total surface area of 88 mm², compared to the surface area of sensors A and B which is of 507 mm². FIGS. 21A to 21D show the capacitance measured as the hand-held probes scan a line directly over the cells containing the contrast agent. The measured probe signal strength is related to both the inhomogeneity permittivity and size. In particular, for the cases in which the injected liquid areas are smaller than the inner disc of the concentric sensor, two peaks in the output signal are observed for each measurement, due to the sensor gaps on each side of the sensor responding to the inhomogeneity separately. On the other hand, when the injected liquid area is greater than the inner electrode size, a single peak in the measurement signal is observed due to both sides of the sensor being excited simultaneously. As can be seen from FIGS. 21A-21D, the approximate size of the inhomogeneity can be inferred from the shape of the measured signal and permittivity information can be extracted from the signal magnitude.

In summary, the outstanding ability of the probes to detect low contrast zones smaller than the sensors themselves has been demonstrated. For example, both sensors detected successfully 1 cc of olive oil ($\epsilon_r \approx 3$) filling 4 cells in the honeycomb core of a laminar structure, indicating their potential application in defect detection in aircraft radome sandwich structures.

aged areas was 2.53±0.03 and for the impact damaged area was 2.54±0.01. This one example suggests that capacitive NDE is not suitable for characterizing impact damage in glass fiber composite.

6.8 Conclusion

Two hand-held capacitive probes with different target penetration depths have been built and tested. Following a calibration procedure that accounts for stray capacitances and the presence of the probe casing, which is not accounted for explicitly in the accompanying model, agreement to within 10% between measured and calculated capacitances has been demonstrated for experiments on laminar structures. The penetration depth of concentric capacitive sensors has been defined and studied both numerically and experimentally. For a given electrode configuration, the sensor penetration depth increases as test-piece permittivity increases. For a given test-piece, sensors with wider electrode spacing have larger penetration depths but lower capacitance values. The hand-held probes' sensitivity to lift-off variations has been assessed numerically and experimentally. In order to acquire inversely determined material permittivities close to the actual values, small lift-off values are desirable because such measurement setups give rise to the best signal strength. This suggests that,

TABLE 3

Measured capacitance of hand-held probes on a Delrin ® slab with contrast zones.

| Hole diameter (mm) | Measured capacitance on air filled holes (pF) | | Relative diff. for air filled holes (%) | | Measured capacitance on wax filled holes (pF) | | Relative diff. for wax filled holes (%) | |
|---|---|---|---|---|---|---|---|---|
| | Sensor A | Sensor B | Sensor A | Sensor B | Sensor A | Sensor B | Sensor A | Sensor B |
| 2.5 | 2.87 | 1.91 | 0.3 | 1.0 | 2.88 | 1.93 | 0.0 | 0.0 |
| 5.0 | 2.85 | 1.89 | 1.0 | 2.1 | 2.87 | 1.92 | 0.3 | 0.5 |
| 7.5 | 2.83 | 1.86 | 1.7 | 3.6 | 2.85 | 1.90 | 1.0 | 1.6 |
| 10 | 2.79 | 1.82 | 3.1 | 5.7 | 2.82 | 1.87 | 2.1 | 3.1 |

The measured capacitances of intact areas are C = 2.88 pF and C = 1.93 pF for sensors A and B, respectively. The relative difference is compared to the intact area capacitances. Uncertainty in measured C is 0.3%.

TABLE 4

Properties of the glassfiber-honecomb-glassfiber sandwich panel

| Parameter | Value |
|---|---|
| Core thickness | 7.62 mm |
| Skin thickness | 0.254 mm |
| Cell volume | 0.25 cc |
| Surface area of cell | 22 mm² |
| Panel length and width | 298.45 mm |

A glass fiber composite with dimensions 13.7 cm×10.2 cm×3.24 mm was impact damaged on both sides by a dropped weight to generate a well-damaged area (of about 1 cm2 on each surface). Broken glass fibers and delamination were observed at the surface on both sides and assumed to exist throughout the whole thickness of the sample. Both sides of the sample where the weight was dropped were machined flat so that the signal of the capacitive sensor was from the internal damage of the composite rather than from the surface indentation.

Capacitive sensors A and B were used to assess the impact-damaged area. The capacitance values were then compared with those of the undamaged regions. For sensor A, the average measured capacitance for undamaged areas was 3.68±0.05 and for the impact damaged area was 3.67±0.02. For sensor B, the average measured capacitance for undamif the probe is to be used for quantitative permittivity measurement, then calibration on a known test sample may be preferable to calibration in air. Experimental results show that the concentric capacitive sensors are unable to effectively characterize impact damage in glass fiber composites. The outstanding capability of the hand-held sensors in detecting relatively small contrast zones in one-layered and multi-layered structures has been demonstrated experimentally, e.g., 1 cc olive oil injection in glassfiber sandwich panel was successfully detected.

The hand-held probes discussed here were built using readily available materials and components. In the future, some refinements can be made to the probe assembly in order to improve the agreement between measurement results and numerical calculations. For example, the probe test fixture and the BNC to receptacle adaptor can be replaced by a combined lead and sensor, thereby reducing parasitic capacitance. Additionally, the lead and sensor can be enclosed in a more compact rigid case that has fewer effects on the sensor signal. Thus, it should be understood that the present invention contemplates numerous variations. In addition, the present invention contemplates variations in the materials used for the sensor, the specific size and geometry of the sensor, the type of structure being tested and the corresponding models for the structures under test. The present invention is not to be limited to the specific details of the embodiments described herein.

REFERENCES

The following references are herein incorporated by reference in their entireties.

[1] J. Baker-Jarvis, C. Jones, B. Riddle, M. Janezic, R. G. Geyer, J. H. Grosvenor, and C. M. Weil, "Dielectric and magnetic measurements: a survey of nondestructive, quasi-nondestructive, and process-control techniques", Research in Nondestructive Evaluation, Vol. 7, pp. 117-136, 1995.

[2] R. N. Clarke and C. B. Rosenberg, "Fabry-Perot and open resonators at microwave and millimeter wave frequencies, 2-300 GHz", J. Phys. E: Sci. Instrum., Vol. 15, pp. 9-24, 1982.

[3] J. Zhao, K. D. Stephan, S. Wong, and R. S. Porter, "Tensor permittivity measurements of thin films of millimeter wavelength", Intern. J. Infrared and Millimeter Waves, Vol. 9, pp. 1093-1105, 1988.

[4] W. Ou, C. G. Gardner, and S. Long, "Nondestructive measurement of a dielectric layer using surface electromagnetic waves", IEEE Trans. Microwave Theory Tech., Vol. 31, pp. 255-261, 1983.

[5] R. Olmi, M. Bini, A. Ignesti, S. Priori, C. Riminesi, and A. Felici, "Diagnostics and monitoring of frescoes using evanescent-field dielectrometry", Meas. Sci. Technol., Vol. 17, pp. 2281-2288, 2006.

[6] R. Comrie, S. Affrossman, D. Hayward, and R. A. Pethrick, "Nondestructive examination of epoxy adhesive-bonded structures exposed to a humid environment: a comparison of low- and high-frequency dielectric measurements", J. Adhesion, Vol. 78, pp. 967-985, 2002.

[7] A. V. Mamishev, K. Sundara-Rajan, F. Yang, Y. Du, and M. Zahn, "Interdigital Sensors and Transducers", Proc. IEEE, Vol. 92, pp. 808-845, 2004.

[8] M. C. Zaretsky, L. Mouayad, J. R. Melcher, "Continuum properties from interdigital electrode dielectrometry", IEEE Trans. Electr. Insul., Vol. 23, pp. 897-917, 1988.

[9] A. V. Mamishev, B. C. Lesiecutre and M. Zahn, "Optimization of multiwavelength interdigital dielectrometry instrumentations and algorithms", IEEE Trans. Dielectr. Electr. Insul., Vol. 5, pp. 408-420, 1998.

[10] X. B. Li, S.D. Larson, A. S. Zyuzin, and A. V. Mamishev, "Design principles for multichannel fringing electric field sensors", IEEE Sensors J., Vol. 6, pp. 434-440, 2006.

[11] P. J. Shull, A. V. Clark, P. R. Heyliger, J. C. Moulder, and B. A. Auld, "Characterization of capacitive array for NDE applications", Res. Nondestr. Eval., Vol. 2, pp. 11-27, 1990.

[12] I. C. Shay and M. Zahn, "Cylindrical geometry electroquasistatic dielectrometry sensors", IEEE Trans. Dielectr. Electr. Insul., Vol. 12, pp. 41-49, 2005.

[13] A. A. Nassr, W. H. Ahmed, and W. W. El-Dakhakhni, "Coplanar capacitance sensors for detecting water intrusion in composite structures", Meas. Sci. Technol., Vol. 19, pp. 075702(7 pp), 2008.

[14] A. A. Nassr and W. W. El-Dakhakhni, "Non-destructive evaluation of laminated composite plates using dielectrometry sensors", Smart Mater. Struct., Vol. 18, pp. 055014 (8 pp), 2009.

[15] I. Bord, P. Tardy, and F. Menil, "Influence of the electrodes configuration on a differential capacitive rain sensor performances", Sensors and Actuators B, Vol. 114, pp. 640-645, 2006.

[16] P. Linderholm, J. Vannod, Y. Barrandon, and P. Renaud, "Bipolar resistivity profiling of 3D tissue culture", Biosensors and Bioelectronics, Vol. 22, pp. 789-796, 2007.

[17] W. Q. Yang and L. Peng, "Image reconstruction algorithms for electrical capacitance tomography", Meas. Sci. Technol., Vol. 14, pp. R1-R13, 2003.

[18] W. Q. Yang, "Hardware design of electrical capacitance tomography systems", Meas. Sci. Technol., Vol. 7, pp. 225-232, 1996.

[19] S. M. Huang, C. G. Xie, R. Thorn, D. Snowden, and M. S. Beck, "Design of sensor electronics for electrical capacitance tomography", IEEE Proc.-G, Vol. 39, pp. 83-88, 1992.

[20] L. Peng, C. Mou, D. Yao, B. Zhang and D. Xiao, "Determination of the optimal axial length of the electrode in an electrical capacitance tomography sensor", Flow Measurement and Instrumentation, Vol. 16, pp. 169-175, 2005.

[21] K. J. Scott, "Electrostatic potential Green's function for multi-layered dielectric media", Philips J. Research, Vol. 45, pp. 293-324, 1990.

[22] J. D. Jackson, *Classical Electrodynamics*, Chap. 3, John Wiley & Sons, Inc., third edition, 1999.

[23] R. F. Harrington, *Field Computation by Moment Methods*, Willey-IEEE Press, 1993.

[24] Chen, T., J. M. Song, J. R. Bowler, and N. Bowler, "Analysis Of A Concentric Coplanar Capacitive Sensor Using A Spectral Domain Approach", *Review of Progress in Quantitative Nondestructive Evaluation*, Volume 1335, pp. 1647-1654.

What is claimed is:

1. A concentric coplanar capacitive sensor system, comprising:
   a concentric coplanar capacitive sensor comprising (a) a charged central disc forming a first electrode, (b) an outer annular ring coplanar with and outer to the charged central disc, the outer annular ring forming a second electrode, (c) a gap between the charged central disc and the outer annular ring, and
   (d) the first electrode and the second electrode attached to an insulative film;
   a capacitance measuring circuit electrically connected to the concentric coplanar capacitive sensor for measuring transcapacitance between the first electrode and the second electrode for use in evaluating a dielectric test piece;
   a processor operatively connected to the first electrode, the processor configured to use the transcapacitance as an input to a quantitative model of the dielectric test piece to determine inversely properties of the dielectric test piece;
   wherein the quantitative model provides a quantitative relationship between a transcapacitance measured with the concentric coplanar capacitive sensor and permittivity and thickness of each of a plurality of layers in the dielectric test piece.

2. The concentric coplanar capacitive sensor system of claim 1 wherein the first electrode and the second electrode being formed of copper.

3. The concentric coplanar capacitive sensor system of claim 1 wherein the charged central disc and outer annular ring provide rotational symmetry.

4. The concentric coplanar capacitive sensor system of claim 1 wherein the first electrode and the second electrode being electrically connected to a capacitance measuring circuit for measuring transcapacitance between the first electrode and the second electrode.

5. A rotationally invariant hand-held capacitive probe, comprising the concentric coplanar capacitive sensor system of claim 1.

6. The system of claim 1 wherein the dielectric test piece is a multi-layered planar dielectric structure.

7. The system of claim 1 wherein the dielectric test piece is a multi-layered cylindrical dielectric structure with radius larger than the outer radius of the sensor by at least a factor of 3.

8. The system of claim 1 wherein the dielectric test piece is a radome structure.

9. The system of claim 1 wherein the dielectric test piece is a radome structure and wherein the processor is configured to use the transcapacitance to detect water or excessive inhomogeneities caused by repairs in the radome structure.

10. The system of claim 1 wherein the dielectric test piece is a radome structure and wherein the processor is configured to use the transcapacitance to detect inhomogeneities in the radome structure.

11. The system of claim 10 wherein the inhomogeneities being caused by at least one of repair to the radome structure or impact damage.

12. The system of claim 1 further comprising a housing, the capacitance measuring circuit and the processor disposed within the housing.

13. The system of claim 12 further comprising a display electrically connected to the processor, the display operatively connected to the housing.

14. The system of claim 13 wherein the housing is a handheld housing.

15. A method of non-destructive evaluation, the method comprising:
   providing a concentric coplanar capacitive sensor;
   providing a quantitative model for the concentric coplanar capacitive sensor wherein the model provides a quantitative relationship between a transcapacitance measured with the concentric coplanar capacitive sensor and permittivity and thickness of each of a plurality of layers in a dielectric test piece;
   attaching the concentric coplanar capacitor sensor to the dielectric test piece;
   applying an input signal across the concentric coplanar capacitive sensor to produce an output signal;
   determining transcapacitance between the first electrode and the second electrode based on the output signal; and
   using the transcapacitance in the quantitative model to determine inversely properties of the dielectric test piece.

16. The method of claim 15 wherein the dielectric test piece comprises a plurality of dielectric layers.

17. The method of claim 15 wherein the dielectric test piece comprises a multiple layer aircraft radome structure.

18. The method of claim 15 wherein the properties include a dielectric constant for each layer of a plurality of layers of the dielectric test piece.

19. The method of claim 15 wherein the properties include thickness for each layer of a plurality of layers of the dielectric test piece.

20. The method of claim 15 wherein the properties of the dielectric test piece include water in the dielectric test piece.

21. The method of claim 15 where the properties include inhomogeneities in the dielectric test piece.

* * * * *